US009109249B2

(12) United States Patent
Naser et al.

(10) Patent No.: US 9,109,249 B2
(45) Date of Patent: Aug. 18, 2015

(54) MICROBE DETECTION VIA HYBRIDIZING MAGNETIC RELAXATION NANOSENSORS

(75) Inventors: Saleh Naser, Orlando, FL (US); J. Manuel Perez, Orlando, FL (US); Charalambos Kaittanis, New York, NY (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

(21) Appl. No.: 14/118,834

(22) PCT Filed: May 21, 2012

(86) PCT No.: PCT/US2012/038903
§ 371 (c)(1),
(2), (4) Date: Apr. 14, 2014

(87) PCT Pub. No.: WO2012/159121
PCT Pub. Date: Nov. 22, 2012

(65) Prior Publication Data
US 2014/0220565 A1   Aug. 7, 2014

Related U.S. Application Data

(60) Provisional application No. 61/487,977, filed on May 19, 2011.

(51) Int. Cl.
*C12Q 1/68* (2006.01)
*C07H 21/02* (2006.01)

(52) U.S. Cl.
CPC .............. *C12Q 1/6825* (2013.01); *C12Q 1/689* (2013.01); *C12Q 1/6816* (2013.01)

(58) Field of Classification Search
CPC .... C12Q 1/6813; C12Q 1/6816; C12Q 1/689; C12Q 1/6876; C07H 21/00
USPC .............. 435/6.1, 283.1; 536/22.1, 23.1, 24.3
See application file for complete search history.

(56) References Cited

U.S. PATENT DOCUMENTS

| | | | |
|---|---|---|---|
| 5,660,990 | A | 8/1997 | Rao |
| 6,361,940 | B1 * | 3/2002 | Van Ness et al. ............ 435/6.12 |
| 6,661,221 | B2 | 12/2003 | Taguchi |
| 6,891,368 | B2 | 5/2005 | Kawano |
| 7,531,149 | B2 | 5/2009 | Peng |
| 8,409,463 | B1 | 4/2013 | Perez |
| 2002/0151787 | A1 | 10/2002 | Bjornerud |
| 2003/0124194 | A1 | 7/2003 | Gaw |
| 2004/0086885 | A1 | 5/2004 | Lee |
| 2005/0130167 | A1 * | 6/2005 | Bao et al. .......................... 435/6 |
| 2006/0275757 | A1 | 12/2006 | Lee |
| 2006/0286379 | A1 | 12/2006 | Gao |
| 2007/0090323 | A1 | 4/2007 | Duguet |
| 2010/0072994 | A1 | 3/2010 | Lee |
| 2011/0021374 | A1 | 1/2011 | Lee |
| 2013/0330280 | A1 | 12/2013 | Perez |

FOREIGN PATENT DOCUMENTS

| | | |
|---|---|---|
| EP | 1260595 | 11/2002 |
| EP | 0805343 | 7/2003 |
| EP | 1458031 | 1/2005 |
| EP | 1631318 | 11/2010 |
| WO | WO 03/072830 | 9/2003 |
| WO | WO 2004/003508 | 1/2004 |
| WO | WO 2004/083902 | 9/2004 |
| WO | WO 2007/027843 | 3/2007 |
| WO | WO 2009/085214 | 7/2009 |
| WO | WO 2012/159121 | 11/2012 |

OTHER PUBLICATIONS

Corti et al. Detection of Mycobacterium avium subspecies paratuberculosis specific IS900 insertion sequences in bulk-tank milk samples obtained from different regions throughout Switzerland. BMC Microbiology 2:15 pp. 1-7 (2002).*
Baghi M, et al. (2005) The efficacy of MRI with ultrasmall superparamagnetic iron oxide particles (USPIO) in head and neck cancers. Anticancer Res. 25: 3665-3670.
Corr SA, et al. (2008) From Nanocrystals to Nanorods: New Iron Oxide—Silica Nanocomposites from Metallorganic Precursors. 112: 1008-1018.
Culp JT, et al. (2003) Monolayer, bilayer, multilayers: evolving magnetic behavior in Langmuir-Blodgett films containing a two-dimensional iron-nickel cyanide square grid network. Inorg Chem. 42: 2842-2848.
Enpuka K. (2005) Magnetic immunoassay with SQUID and magnetic marker. Digests of the IEEE International. 413-415.
Fazzina D. (2007) 7347-Facile Synthesis of Highly Magnetic Polymer Coated Iron Oxide Particles for Sensing Applications. NERAC, Inc. Research Report No. 10032825 (Tolland, CT) (2 pages).
Fujii T, et al. (1999) In situ XPS analysis of various iron oxide films grown by NO2-assisted molecular-beam epitaxy. Phys Rev. 59: 3195-9202.
Gao LZJ, et al. (2007) Intrinsic peroxidase-like activity of ferromagnetic nanoparticles. Nat Nanotechnol. 2: 577-583.
Gass J, et al. (2006) Superparamagnetic Polymer Nanocomposites with Uniform Fe3O4 Nanoparticle Dispersions. Advanced Functional Materials. 16: 71-75.
Goya GFB, et al. (2003) Static and dynamic magnetic properties of spherical magnetite nanoparticles. J Appl Phys. 94: 3520.
Gupta AK and Curtis AS. (2004) Surface modified superparamagnetic nanoparticles for drug delivery: interaction studies with human fibroblasts in culture. J Mater Sci Mater Med. 15: 493-496.

(Continued)

Primary Examiner — Ethan C Whisenant
(74) Attorney, Agent, or Firm — Ballard Spahr LLP

(57) ABSTRACT

Disclosed herein are methods and materials for facilitating the detection of nucleic acid analytes of interest. Specifically exemplified herein are methods for detecting mycobacterial microorganisms, namely *Mycobacterium avium* spp. *paratuberculosis*. Also disclosed is new hybridizing magnetic relaxation nanosensor (hMRS) particularly adapted to detect a target nucleic acid analyte of interest.

18 Claims, 7 Drawing Sheets

(56) References Cited

OTHER PUBLICATIONS

Gupta AK, et al. (2005) Synthesis and surface engineering of iron oxide nanoparticles for biomedical applications. Biomaterials. 26: 3995-4021.

Hellstern D, et al. (2006) Systemic distribution and elimination of plain and with Cy3.5 functionalized poly(vinyl alcohol) coated superparamagnetic maghemite nanoparticles after intraarticular injection in sheep in vivo. J Nanosci Nanotechnol. 6: 3261-3268.

Hu J, et al. (2001) Linearly polarized emission from colloidal semiconductor quantum rods. Science. 292: 2060-2063.

Ito A, et al. (2004) Magnetite nanoparticle-loaded anti-HER2 immunoliposomes for combination of antibody therapy with hyperthermia. Cancer Lett. 212: 167-175.

Jaiswal JK, et al. (2004) Synaptotagmin VII restricts fusion pore expansion during lysosomal exocytosis. PLoS Biol. 2: E233.

Jiang W, et al. (2004) Preparation and properties of superparamagnetic nanoparticles with narrow size distribution and biocompatible. Journal of Magnetism and Magnetic Materials. 283: 210-214.

Josephson L, et al. (1999) High-efficiency intracellular magnetic labeling with novel superparamagnetic-Tat peptide conjugates. Bioconjug Chem. 10: 186-191.

Jun Y, et al. (2005) Nanoscale size effect of magnetic nanocrystals and their utilization for cancer diagnosis via magnetic resonance imaging. J Am Chem Soc. 127: 5732-5733.

Kaittanis C, et al. (2007) One-step, nanoparticle-mediated bacterial detection with magnetic relaxation. Nano Lett. 7: 380-383.

Kaittanis C, et al. (2012) Rapid and sensitive detection of an intracellular pathogen in human peripheral leukocytes with hybridizing magnetic relaxation nanosensors. PLoS One. 7(4):e35326.

Kohler N, et al. (2005) Methotrexate-modified superparamagnetic nanoparticles and their intracellular uptake into human cancer cells. Langmuir. 21: 8858-8864.

Lee H, et al. (2006) Antibiofouling polymer-coated superparamagnetic iron oxide nanoparticles as potential magnetic resonance contrast agents for in vivo cancer imaging. J Am Chem Soc. 128: 7383-7389.

Li W, et al. (2006) Multiamino-functionalized carbon nanotubes and their applications in loading quantum dots and magnetic nanoparticles. J Mater Chem. 16: 1852-1859.

Magana D, et al. (2006) Switching-on superparamagnetism in Mn/CdSe quantum dots. J Am Chem Soc. 128: 2931-2939.

Manna LS, et al. (2000) Synthesis of Soluble and Processable Rod-, Arrow-, Teardrop-, and Tetrapod-Shaped CdSe Nanocrystals. J. Am. Chem. Soc. 122: 12700-12706.

Melosh NA, et al. (2003) Ultrahigh-density nanowire lattices and circuits. Science. 300: 112-115.

Nath S, et al. (2009) Synthesis, magnetic characterization and sensing applications of novel dextran-coated iron oxide nanorods. Chem Mater. 21(8): 1761-1767.

Nath S, et al. (2008) Dextran-coated gold nanoparticles for the assessment of antimicrobial susceptibility. Anal Chem. 80: 1033-1038.

Nedeljkovic D, et al. (2004) Application of Permanent Magnetic Powder for Magnetic Field Sensing Elements. Rom Journ Phys. 50: 971-976.

Park SJ, et al. (2000) Synthesis and Magnetic Studies of Uniform Iron Nanorods and Nanospheres. J Am Chem Soc. 122: 8581-8582.

Peng X, et al. (2000) Shape control of CdSe nanocrystals. Nature. 404: 59-61.

Perez JM, et al. (2002a) Magnetic relaxation switches capable of sensing molecular interactions. Nat Biotechnol. 20: 816-820.

Perez JM, et al. (2002b) DNA-based magnetic nanoparticle assembly acts as a magnetic relaxation nanoswitch allowing screening of DNA-cleaving agents. J Am Chem Soc. 124: 2856-2857.

Perez JM, et al. (2003) Viral-induced self-assembly of magnetic nanoparticles allows the detection of viral particles in biological media. J Am Chem Soc. 125: 10192-10193.

Perez JM, et al. (2004) Use of magnetic nanoparticles as nanosensors to probe for molecular interactions. Chembiochem. 5: 261-264.

Perez JM, et al. (2008) Synthesis of biocompatible dextran-coated nanoceria with pH-dependent antioxidant properties. Small. 4: 552-556.

Perez JM. (2007) Iron oxide nanoparticles: hidden talent. Nat Nanotechnol. 2: 535-536.

Puntes VF, et al. (2001) Colloidal nanocrystal shape and size control: the case of cobalt. Science. 291: 2115-2117.

Radojevic V, et al. (2004) Process of Coating Optical Fiber with Composite Coating: Composite Coating: Magnetic Powder—Polymer. Powder metallurgy; Euro PM2004. 533-538.

Shen T, et al. (1993) Monocrystalline iron oxide nanocompounds (MION): physicochemical properties. Magn Reson Med. 29: 599-604.

Thorek DL, et al. (2006) Superparamagnetic iron oxide nanoparticle probes for molecular imaging. Ann Biomed Eng. 34: 23-38.

Wang DH, et al. (2004) Superparamagnetic $Fe_2O_3$ Beads—CdSe/ZnS Quantum Dots Core—Shell Nanocomposite Particles for Cell Separation. Nano Lett. 4: 409-413.

Wang JP, et al. (2004) Growth of magnetite nanorods along its easy-magnetization axis of [1 1 0]. J Cryst Growth. 263: 616-619.

Zhao YM, et al. (2006) Growth and characterization of iron oxide nanorods/nanobelts prepared by a simple iron-water reaction. Small. 2: 422-427.

Zou G, et al. (2005) $Fe_3O_4$ nanocrystals with novel fractal. J Phys Chem B. 109: 18356-18360.

Non-Final Office Action issued Jun. 9, 2011 for U.S. Appl. No. 12/174,169, filed on Jul. 16, 2008 (Perez et al.—inventors) (11 pages).

Examiner Interview Summary issued Oct. 20, 2011 for U.S. Appl. No. 12/174,169, filed Jul. 16, 2008 (Perez et al.—inventors) (3 pages).

Response to Non-Final Office Action filed Oct. 28, 2011 for U.S. Appl. No. 12/174,169, filed Jul. 16, 2008 (Perez et al.—inventors) (12 pages).

Non-Final Office Action issued Jan. 3, 2012 for U.S. Appl. No. 12/174,169, filed Jul. 16, 2008 (Perez et al.—inventors) (13 pages).

Examiner Interview Summary issued Mar. 6, 2012 for U.S. Appl. No. 12/174,169, filed Jul. 16, 2008 (Perez et al.—inventors) (3 pages).

Informal or Non-Responsive Amendment filed Apr. 27, 2012 for U.S. Appl. No. 12/174,169, filed Jul. 16, 2008 (Perez et al.—inventors) (10 pages).

Notice of Non-Compliant Amendment issued May 2, 2012 for U.S. Appl. No. 12/174,169, filed Jul. 16, 2008 (Perez et al.—inventors) (1 page).

Response to Non-Final Office Action filed Jun. 4, 2012 for U.S. Appl. No. 12/174,169, filed Jul. 16, 2008 (Perez et al.—inventors) (6 pages).

Final Office Action issued Aug. 10, 2012 for U.S. Appl. No. 12/174,169, filed Jul. 16, 2008 (Perez et al.—inventors) (13 pages).

Response to Final Office Action filed Oct. 10, 2012 for U.S. Appl. No. 12/174,169, filed Jul. 16, 2008 (Perez et al.—inventors) (7 pages).

Advisory Action issued Nov. 6, 2012 for U.S. Appl. No. 12/174,169, filed Jul. 16, 2008 (Perez et al.—inventors) (3 pages).

Response to Final Office Action filed Nov. 9, 2012 for U.S. Appl. No. 12/174,169, filed Jul. 16, 2008 (Perez et al.—inventors) (4 pages).

Amendment After Final issued Nov. 30, 2012 for U.S. Appl. No. 12/174,169, filed Jul. 16, 2008 (Perez et al.—inventors) (1 page).

Notice of Allowance and Fee(s) Due issued Nov. 30, 2012 for U.S. Appl. No. 12/174,169, filed Jul. 16, 2008 (Perez et al.—inventors) (5 pages).

Amendment After Notice of Allowance filed Jan. 18, 2013 for U.S. Appl. No. 12/174,169, filed Jul. 16, 2008 (Perez et al.—inventors) (3 pages).

Response to Amendment under Rule 312 issued Feb. 4, 2013 for U.S. Appl. No. 12/174,169, filed Jul. 16, 2008 (Perez et al.—inventors) (4 pages).

Issue Notification issued Mar. 13, 2013 for U.S. Appl. No. 12/174,169, filed Jul. 16, 2008 (Perez et al.—inventors) (1 page).

Preliminary Amendment filed on Apr. 2, 2013 for U.S. Appl. No. 13/855,706, filed Apr. 2, 2013 (Perez et al.—inventors) (7 pages).

(56) References Cited

OTHER PUBLICATIONS

Non-Final Office Action issued Nov. 8, 2013 for U.S. Appl. No. 13/855,706, filed Apr. 2, 2013 (Perez et al.—inventors) (8 pages).
Notice of Panel Decision from Pre-Appeal Brief Review mailed Oct. 23, 2013 for U.S. Appl. No. 12/258,785, filed Oct. 27, 2008 (Inventors—Perez et al.) (2 pages).
Notice of Panel Decision from Pre-Appeal Brief Review mailed Aug. 1, 2013 for U.S. Appl. No. 12/258,785, filed Oct. 27, 2008 (Inventors—Perez et al.) (2 pages).
Pre-Appeal Brief Request for Review filed Jun. 20, 2013 for U.S. Appl. No. 12/258,785, filed Oct. 27, 2008 (Inventors—Perez et al.) (6 pages).
Final Office Action mailed Mar. 20, 2013 for U.S. Appl. No. 12/258,785, filed Oct. 27, 2008 (Inventors—Perez et al.) (13 pages).
Response to Non-Final Office Action filed Nov. 28, 2012 for U.S. Appl. No. 12/258,785, filed Oct. 27, 2008 (Inventors—Perez et al.) (14 pages).
Non-Final Office Action mailed Sep. 28, 2012 for U.S. Appl. No. 12/258,785, filed Oct. 27, 2008 (Inventors—Perez et al.) (21 pages).
Notice of Panel Decision from Pre-Appeal Brief Review mailed Aug. 3, 2012 for U.S. Appl. No. 12/258,785, filed Oct. 27, 2008 (Inventors—Perez et al.) (2 pages).
Pre-Appeal Brief Request for Review filed Jun. 27, 2012 for U.S. Appl. No. 12/258,785, filed Oct. 27, 2008 (Inventors—Perez et al.) (4 pages).
Final Office Action mailed Feb. 27, 2012 for U.S. Appl. No. 12/258,785, filed Oct. 27, 2008 (Inventors—Perez et al.) (9 pages).
Response to Notice of Non-Compliant Amendment filed Sep. 28, 2011 for U.S. Appl. No. 12/258,785, filed Oct. 27, 2008 (Inventors—Perez et al.) (5 pages).
Notice of Non-Compliant Amendment mailed Sep. 6, 2011 for U.S. Appl. No. 12/258,785, filed Oct. 27, 2008 (Inventors—Perez et al.) (2 pages).
Response to Non-Final Office Action filed Aug. 29, 2011 for U.S. Appl. No. 12/258,785, filed Oct. 27, 2008 (Inventors—Perez et al.) (11 pages).
Non-Final Office Action mailed Apr. 28, 2011 for U.S. Appl. No. 12/258,785, filed Oct. 27, 2008 (Inventors—Perez et al.) (6 pages).
Response to Notice of Non-Compliant Amendment filed Feb. 18, 2011 for U.S. Appl. No. 12/258,785, filed Oct. 27, 2008 (Inventors—Perez et al.) (5 pages).
Notice of Non-Compliant Amendment mailed 1/24/100 for U.S. Appl. No. 12/258,785, filed Oct. 27, 2008 (Inventors—Perez et al.) (2 pages).
Response to Restriction Requirement filed Jan. 20, 2011 for U.S. Appl. No. 12/258,785, filed Oct. 27, 2008 (Inventors—Perez et al.) (6 pages).
Restriction Requirement mailed Dec. 20, 2012 for U.S. Appl. No. 12/258,785, filed Oct. 27, 2008 (Inventors—Perez et al.) (5 pages).
International Preliminary Report on Patentability issued Nov. 28, 2013 for PCT Application No. PCT/US2012/038903 filed May 21, 2012 and published as WO 2012/159121 on 11/122/2012 (Inventors—Perez et al. // Applicant—University of Central Florida Research Foundation) (5 pages).
International Search Report issued Jan. 28, 2013 and published as WO 2012/159121 on 11/122/2012 (Inventors—Perez et al. // Applicant—University of Central Florida Research Foundation) (4 pages).
Written Opinion issued Jan. 28, 2013 and published as WO 2012/159121 on 11/122/2012 (Inventors—Perez et al. // Applicant—University of Central Florida Research Foundation) (4 pages).
Charalambos Kaittanis, et al., The assembly state between magnetic nanosensors and their targets orchestrates their magnetic relaxation response. Journal of the American Chemical Society, vol. 133, No. 10, pp. 3668-3676 (2011).
European Search Report issued Nov. 6, 2014 for European Application No. 12785893.4, filed May 21, 2012 and published as EP 2710151 (Applicant: Univ. of Central FL. Research Foundation, Inc. // First Named Inventor: Saleh Nasser // (7 pages).

* cited by examiner

MICROBE DETECTION VIA HYBRIDIZING MAGNETIC RELAXATION NANOSENSORS

The Sequence Listing submitted on Nov. 20, 2014 as a text file named "26150_0051U2_Sequence_Listing.txt," created on Nov. 20, 2014, and having a size of 741 bytes is hereby incorporated by reference pursuant to 37 C.F.R. §1.52(e)(5).

BACKGROUND

Pathogenesis caused by intracellular pathogens, such as *Mycobacterium tuberculosis* among others, relies on the survival of the microorganism within host cells, such as macrophages and dendritic cells. This mode of infection with or without clinical symptomology hampers bacterial detection, preventing correct diagnosis. Consequently, the physician cannot proceed to the assignment of an appropriate treatment course, delaying the clearance of the pathogen from the body. Serological immunoassays cannot effectively detect intracellular pathogens in biological fluids (e.g. blood, lymphatic fluid) as the microorganism is hidden away within the immune cells. For this reason, isolation of the infected cells and extraction of their DNA, followed by detection of specific bacterial genomic markers via Polymerase Chain Reaction (PCR), is needed to facilitate identification of the pathogen. Although highly specific and sensitive, PCR methods are generally laborious, time-consuming and typically require homogeneous and pure DNA samples [1]. Evidently, complex biological samples, such as biopsies and blood, have to be thoroughly processed in multistep elaborate protocols to obtain pure DNA samples, significantly increasing the final readout time, and affecting the overall DNA yield. An alternative way to detect intracellular pathogens, particularly when they are in low numbers, is by isolating the infected leukocytes from the blood and expanding the number of viable bacteria via culturing methods before PCR analysis. Although very effective, bacterial culturing methods require a significant amount of time, such as in the case of slow-growing intracellular pathogens that have to be cultivated for even weeks, assuming that there is an adequate amount of viable pathogens in the clinical sample. Another drawback of culturing methods is that some pathogens do not grow effectively in culture, either because of the nature of the pathogen itself or the presence of biological interferences present in the clinical sample that prevent growth in culture. Because of these hurdles, new technologies that can detect the presence of a pathogen in human clinical samples are urgently needed.

It has been predicted that nanotechnology will have a major impact in medicine, agriculture and biotechnology among other fields [2], [3], [4], [5], [6], [7], [8], [9], [10]. Innovative technologies that take advantage of the unique size-dependent electronic, magnetic and luminescence properties that some nanomaterials exhibit when they specifically interact with a biological marker have been developed for faster and more accurate sensing of various pathogens [2], [3], [4], [5]. However, the translation of these technologies to the clinical diagnosis of an infectious disease and how it relates to the presence of the pathogen in clinical samples has been limited. The slow clinical translation of some of these nanotechnologies has been partly due to their poor performance in crude or minimally processed clinical samples. Among the most promising nanomaterials are magnetic relaxation nanosensors (MRS). These magnetic nanosensors are composed of a polymer-coated iron oxide nanoparticle onto which affinity ligands are conjugated to facilitate binding and magnetic detection of a particular target [11], [12]. Upon specific binding of a target to ligands on the magnetic nanoparticle, changes in the sample's magnetic resonance signal (specifically the water proton relaxation time; T2) occur that correlate with the target concentration in solution. By measuring the changes in T2 relaxation times upon target interaction and correlating the intensity of the change with the target concentration, one can develop a sensitive detection method, therefore the acronym of magnetic relaxation nanosensors (MRS).

In contrast to other methods that utilize magnetic nanoparticles as labels and directly measure an intrinsic physical property, such as a magnetic field [13], [14], or a chemical property [6], the MRS method relies on the effect that the nanoparticle's induced magnetic field exerts on the hundreds of thousands of water molecules surrounding the nanoparticle. This effect results in an amplification of the signal, allowing for sensitive detection even in turbid and minimally processed samples, without the need of further amplification, which is critical for assays such as PCR and ELISA. Hence, MRS-based assays can be more affordable than traditional assays, since they use a single reagent that can be easily produced in large quantities, and a single-step that avoids time- and labor-consuming procedures. Additionally, MRS can detect their targets at various point-of-care settings, since the nanosensors are stable at ambient conditions and utilize deployable instrumentation. Recently reported is a unique MRS nanoparticle-target interaction that resulted in rapid T2 increases upon target binding [12]. This unique nanoparticle-target interaction is different from other MRS-based methods, because clustering of the nanoparticles is not required to achieve detection. In contrast, binding of MRS to the target caused fast, target-concentration-dependent increases in T2. Kinetic studies also revealed that the binding of MRS was faster and more sensitive than the MRS clustering, while achieving lower detection thresholds. In addition, nanoparticle valency—the amount of a targeting ligand on the surface of the nanoparticle—plays a role in the magnetic relaxation response. Nanoparticle valency controls the trend of the change in the spin-spin relaxation time ($\Delta T2$). Specifically, it has been found that low valency results in decreases in the $\Delta T2$ as the target concentration increases, while at high valency conditions the $\Delta T2$ increases as the target concentration increases.

SUMMARY

Disclosed herein are materials and methods that take into consideration the faster detection kinetics of MRS binding-based detection assays and the higher sensitivity of the MRS low-valency nanoparticle system. In one embodiment, disclosed is a newly developed nanosensor, hybridizing MRS (hMRS), that switches (increases) the sample's water proton relaxation times (T2) upon binding to a unique genomic marker (e.g. microbial). According to one example, the hMRSs were designed to bind to a specific genomic marker in *Mycobacterium avium* spp. *paratuberculosis* (MAP); an intracellular pathogen known to cause Johne's disease in cattle [15] and has been also implicated in the cause of Crohn's disease in humans [16]. Furthermore, acknowledging the limitations of PCR in detecting nucleic acid biomarkers of intracellular pathogens in clinical samples, the hMRS performance in detecting MAP was examined in human peripheral blood samples of Crohn's disease patients as well as animal tissues with Johne's disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DESCRIPTION OF SUPPLEMENTARY TABLES

Figure 1:
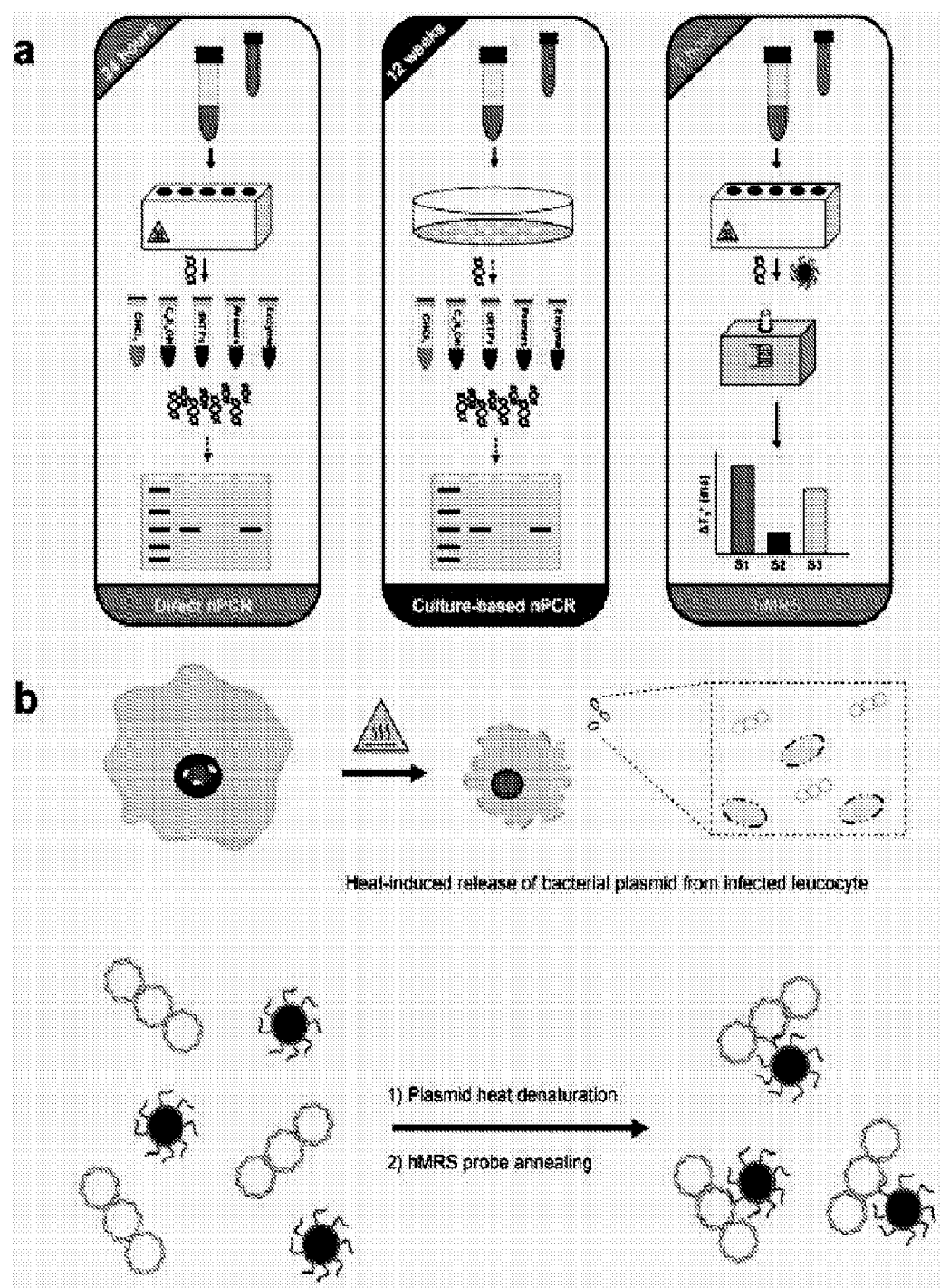
FIG. 1 Design of a nanoparticle-based assay for the identification of genomic markers of the intracellular pathogen *Mycobacterium avium* spp. *paratuberculosis* (MAP). (a) Isolation of MAP requires collection of infected white bloods cells from blood samples via centrifugation. For direct nPCR analysis, DNA directly isolated from white blood cells is purified in multiple steps prior to amplification and detection by gel electrophoresis. Meanwhile, culture-based nPCR requires the growth of MAP in specialized liquid media for 12 weeks, followed by DNA isolation before nPCR. Hybridizing magnetic relaxation sensors (hMRS) can detect MAP DNA in minimally processed blood samples via changes in magnetic signal ($\Delta T2$) in 1 hour, as opposed to 24 hours for direct nPCR and 12 weeks for culture nPCR. (b) Preparation of MAP DNA for hMRS. Heating of infected leucocytes facilities rupture of the cell membrane releasing MAP DNA. Further heating and cooling steps facilitates the annealing and binding of a MAP specific hMRS, resulting in an increase in the $T_2$ water relaxation time.

Table S1 Spin-spin relaxation times (T2) of crude MAP DNA samples. Serial dilutions of crude MAP DNA samples have been utilized to assess the sensitivity of the hMRS method in minimally processed bacterial cultures. The averages of each independent experiment are listed and the studies' mean.

Table S2 Spin-spin relaxation times (T2) of pure MAP DNA samples with known genome copies. Three independent experiments were performed on pure DNA samples obtained from cultured MAP. Correlation between DNA levels and bacterial populations was achieved by quantifying DNA spectrophotometrically and using the MAP genome size as a reference.

Table S3 Demographics of cultured clinical isolates that were screened with hMRS and nPCR. (CD: Crohn's disease, IBD: inflammatory bowel disease)

Table S4 Clinical data and hMRS results of Cohort 1 blood samples. Samples from Crohn's disease (CD) patients, healthy individuals or asymptomatic carriers were analyzed by direct nPCR and hMRS. Quantification of the MAP genome copies was achieved in positive (+) samples using a training standard curve for crude extracted MAP DNA.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Bacterial infections are a major global healthcare problem, and their detection has to be performed in diverse settings and samples preferably with single-instrument-based diagnostic modalities, using sensitive and robust probes. Acknowledging these concerns, hybridizing magnetic nanosensors (hMRS) were used for the detection of the intracellular slow-growing pathogen *Mycobacterium avium* spp. *paratuberculosis* (MAP) that resides in peripheral macrophages, through the identification of its unique genomic signature. Clinically relevant samples, including tissue and blood, were screened with hMRS and gold standard PCR assays. Within less than an hour, the hMRS identified MAP-positive samples in a library of laboratory cultures, clinical isolates, blood and homogenized tissues. Comparison of the hMRS with PCR methodologies in terms of prediction of disease state revealed that the hMRS outperformed the other assays, while being significantly faster (1 hour vs 12 weeks). Additionally, using a single instrument detection of the intracellular bacterial target in clinical samples was possible at the genomic and epitope levels. There are, therefore, clinical and field uses of the hMRS in the multiplexed identification of microbial pathogens and other disease-related biomarkers via a single instrument in clinical and complex environmental samples, for which the use in detecting MAP and its correlation with a disease such as diabetes is one example.

MAP is found within the white blood cells of infected animals with Johne's disease, a form of animal *paratuberculosis*, which is associated with chronic enteritis, reminiscent of Crohn's disease in humans [16]. As early as 1913, Dalziel noted the clinical similarities of animal *paratuberculosis*, intestinal tuberculosis and human chronic granulomatous enteritis (Crohn's disease) [17]. In humans, Crohn's disease is a debilitating chronic inflammatory syndrome of the gastrointestinal track and adjacent lymph nodes [17], [18], [19]. The detection of MAP in tissues from patients with Crohn's disease has been extensively reported. Of particular importance to our study is the report of the presence of MAP in human peripheral blood [20], [21], [22]. In those studies, MAP was identified by a culture method followed by PCR identification of a MAP genomic marker. The whole process took several months to complete, due to the slow growing nature of this pathogen. Such a slow detection method not only delays the diagnosis, but also slows any potential therapeutic intervention [20], [21]. Likewise, difficulties in detecting an intracellular pathogen, such as MAP, hamper studies aimed at the investigation of the potential role of MAP in Crohn's disease pathology, as well as the pathogen's impact on the dairy and beef industries.

Attracted by MAP's slow growing characteristics, intracellular residence and clinical and agricultural relevance, hMRS was used for the identification of a highly conserved MAP genomic element (IS900). This unique DNA insertion sequence has been previously used to identify MAP in clinical samples and cultures by PCR, as it has not been found in other microorganisms or mycobacteria [23], [24], [25]. Detection is primarily achieved through either direct or culture-based nested PCR (nPCR), which use pure DNA extracts from infected leukocytes. Both PCR methods sequentially amplify a 398 bp fragment (amplification round 1) and a 298 bp internal sequence (amplification round 2). It was reasoned that the binding of hMRS to IS900 would achieve faster and more sensitive detection of MAP DNA via magnetic relaxation in minimally processed clinical samples. Initial studies revealed that hMRS can specifically detect MAP's genomic marker without showing cross-reactivity with other mycobacteria. Furthermore, the presence of MAP in homogenized tissues from Johne's disease cattle was achieved at the genomic and epitope levels using hMRS and anti-MAP antibody-carrying MRS, demonstrating that the MRS technology can achieve detection at the genome and organism levels using diverse molecular probes. Finally, a library of 60 blood samples from Crohn's disease patients and healthy individuals was screened with hMRS and nPCR assays. Using minimally processed blood samples, within 60 minutes the hMRS were able to detect the intracellular pathogen and better predict the clinical condition of an individual (healthy vs Crohn's disease) than the nPCR methodologies. Specifically, hMRS outperformed the 12-week-long culture-based nPCR in clinical prognosis, as well as the least reliable direct nPCR, which are currently used in clinical and research studies. Overall, the present disclosure demonstrates for the first time the use and validation of a novel translational nanotechnology, where the unique water relaxation properties of iron oxide nanoparticles and the dynamics of the nanoparticle/target interaction were harnessed to achieve a sensitive genomic biomarker detection system for an intracellular pathogen in samples directly obtained from human patients.

As used herein, a "sample" or "test sample" can include, but is not limited to, biological material obtained from an organism or from components of an organism, food sample, or environmental sample (e.g. water sample or any other sample from an environmental source believed to contain a microorganism). The test sample may be of any biological tissue or fluid, for example. In some embodiments, the test sample can be a clinical sample derived from a patient. Examples of test samples include, but are not limited to sputum, cerebrospinal fluid, blood, blood fractions such as serum and plasma, blood cells, tissue, biopsy samples, urine, peritoneal fluid, pleural fluid, amniotic fluid, vaginal swab, skin, lymph fluid, synovial fluid, feces, tears, organs, or tumors. A test sample can also include recombinant cells, cell components, cells grown in vitro, and cell culture constituents including, for example, conditioned medium resulting from the growth of cells in cell culture medium.

According to one embodiment, a method of detecting a nucleic acid analyte of interest in a sample is provided. The method includes subjecting nucleic acid from the sample with at least one hybridizing magnetic relaxation nanosensor (hMRS), wherein said hMRS is configured to specifically hybridize to the nucleic acid analyte of interest. The method further includes detecting a change in the magnetic resonance signal from a hMRS hybridized to a nucleic acid analyte of interest in the nucleic acid from the sample; thereby detecting the presence of the nucleic acid analyte of interest in the sample. In a specific embodiment, the at least one hMRS pertains to a population of hMRS configured to specifically hybridize to the nucleic acid analyte of interest. In another specific embodiment, nucleic acid is isolated from the sample prior to the subjecting step, to obtain isolated nucleic acid. Thus, in this specific example, the hMRS is applied to the isolated nucleic acid.

In another specific example, the nucleic acid analyte of interest is of a microorganism. In a more specific example, the microorganism is a *mycobacterium*. In an even more specific embodiment, the microorganism is a strain of *Mycobacterium avium* spp. *paratuberculosis*. One specific example of a nucleic acid analyte is IS900.

In a typical example, the hMRS includes a magnetic nanoparticle. The magnetic nanoparticle is typically is comprised of metal and/or metal oxide.

According to another embodiment, provided is a hybridizing magnetic relaxation nanosensor that includes a magnetic nanoparticle associated with a nucleic acid that is configured to specifically hybridize to a nucleic acid analyte of interest. In a typical example, the nucleic acid analyte of interest is of a microorganism. In a specific example, the microorganism is *Mycobacterium avium* spp. *paratuberculosis*.

Another embodiment disclosed is a method of distinguishing a mycobacterial related bowel condition from a non-mycobacterial related bowel condition in a patient exhibiting symptoms of a bowel condition. In a specific example, the mycobacterial related bowel condition is inflammatory bowel disease (IBD). In an even more specific example, the bowel condition is Crohn's disease. A patient exhibiting symptoms of a bowel condition typically will exhibit one or more of the following symptoms: abdominal pain, vomiting, diarrhea, rectal bleeding, severe internal cramps/muscle spasms in the region of the pelvis, weight loss and various associated complaints or diseases like arthritis, pyoderma gangrenosum, porridge-like stool, and primary sclerosing cholangitis.

Typically, a method of distinguishing the conditions involves (a) subjecting nucleic acid from a sample obtained from the patient with at least one hybridizing magnetic relaxation nanosensor (hMRS), wherein said hMRS is configured to specifically hybridize to a nucleic acid analyte of interest of *Mycobacterium avium* spp. *paratuberculosis*; and detecting a change in the magnetic resonance signal from a hMRS hybridized to a nucleic acid analyte of interest in the nucleic acid from the sample; wherein a change in the magnetic resonance signal indicates that the patient has a mycobacterial related bowel condition. Upon determining that the bowel condition is a mycobacterial related bowel condition, a therapeutically effective amount of an antibiotic composition can be administered to the patient. Examples of such antibiotics, include, but are not limited to, metronidazole, ciprofloxacin, rifaximin, rifabutin, clarithromycin, and metronidazole/ciprofloxacin combination, vancomycin, azathioprine, infliximab, tobramycin, or combinations of any of the foregoing.

The term "microorganism" as used herein is intended to include a virus, bacteria or fungi organism.

Hybridizing Magnetic Relaxation Nanosensors (hMRS)

In some embodiments, the hMRS includes a capture probe associated with a magnetic responsive particle. Typically, the capture probe pertains to a nucleic acid. As used herein with respect to a nucleic acid capture probe, "nucleic acid" refers to deoxyribonucleic acid (DNA) or ribonucleic acid (RNA) and known analogs, derivatives, or mimetics thereof. A nucleic acid capture probe can be oligomeric and include oligonucleotides, oligonucleosides, oligonucleotide analogs, oligonucleotide mimetics and chimeric combinations of these. A nucleic acid capture probe can be single-stranded, double-stranded, circular, branched, or hairpin and can contain structural elements such as internal or terminal bulges or loops.

In some embodiments, a nucleic acid capture probe can have a length of at least, or at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleobases, or the nucleic acid capture probe can have a length within any range bounded by two of the above-mentioned lengths.

In several embodiments, a nucleic acid capture probe and a nucleic acid analyte of interest bind to form a duplex. Such binding may occur through hybridization. As used herein, "hybridization" means the pairing of complementary strands of a nucleic acid capture probe and a nucleic acid analyte of interest. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of a nucleic acid capture probe and nucleic acid analyte of interest.

In some embodiments, a nucleic acid capture probe and nucleic acid molecule of interest can hybridize under "stringent conditions," which refer to conditions under which a nucleic acid capture probe will hybridize to a nucleic acid molecule of interest, but to a minimal number of other sequences. A person of ordinary skill in the art will appreciate that stringent conditions are sequence-dependent and will vary in different circumstances. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C.

"Complementarity," as used herein, refers to the capacity for precise pairing between two nucleobases of a nucleic acid capture probe and nucleic acid analyte of interest. For example, if a nucleobase at a certain position of a capture probe is capable of hydrogen bonding with a nucleobase at a certain position of a nucleic acid analyte of interest, then the position of hydrogen bonding between the capture probe and the nucleic acid analyte of interest is considered to be a complementary position. The capture probe and the analyte of interest are complementary to each other when a sufficient number of complementary positions in each molecule are occupied by nucleobases which can hydrogen bond with each other. Thus, in some embodiments a nucleic acid capture probe and nucleic acid analyte of interest are specifically hybridizable and complementary, which indicate a sufficient degree of precise pairing or complementarity over a sufficient number of nucleobases such that stable and specific binding occurs.

It will be appreciated that the sequence of a nucleic acid capture probe need not be 100% complementary to that of a nucleic acid analyte of interest to be specifically hybridizable. Moreover, a nucleic acid capture probe may hybridize over one or more segments such that intervening or adjacent segments are not involved in the hybridization event (e.g., a loop structure, mismatch or hairpin structure). The nucleic acid capture probes of several embodiments can comprise at least 70%, or at least 75%, or at least 80%, or at least 85%, or at least 90%, or at least 92%, or at least 95%, or at least 97%, or at least 98%, or at least 99% sequence complementarity to a region within the nucleic acid sequence of the analyte of interest. The degree of complementarity to be specifically hybridizable can be selected according to well-known principles of hybridization and in accordance with the intended analytical procedure.

In several embodiments, a nucleic acid capture probe can comprise one or more oligonucleotide mimetics. The term "mimetic" includes oligomeric nucleic acids wherein the furanose ring or the furanose ring and the internucleotide linkage are replaced with non-naturally occurring groups.

In certain embodiments, a nucleic acid capture probe comprises a peptide nucleic acid (PNA) oligonucleotide mimetic (Nielsen et al., Science, 1991, 254, 1497-1500). PNAs have favorable hybridization properties, high biological stability and are electrostatically neutral molecules. In PNA oligonucleotide mimetics, the sugar-backbone of an oligonucleotide is replaced with an amide containing backbone, in particular an aminoethylglycine backbone. The nucleobases are bound directly or indirectly to aza nitrogen atoms of the amide portion of the backbone. Representative U.S. patents that teach the preparation of PNA oligomeric compounds include U.S. Pat. Nos. 5,539,082; 5,714,331 and 5,719,262. PNA compounds can be obtained commercially from Applied Biosystems (Foster City, Calif., USA). Numerous modifications to the basic PNA backbone are known in the art and can be used in several embodiments.

Another class of oligonucleotide mimetic that can be used for nucleic acid capture probes in several embodiments is linked morpholino units (morpholino nucleic acid) having heterocyclic bases attached to the morpholino ring. A number of linking groups have been reported that link the morpholino monomeric units in a morpholino nucleic acid. Morpholino-based oligomeric compounds are non-ionic mimetics of oligonucleotides which are less likely to form undesired interactions with cellular proteins (Dwaine A. Braasch and David R. Corey, Biochemistry, 2002, 41(14), 4503-4510). The morpholino class of oligomeric compounds has been prepared with a variety of different linking groups joining the monomeric subunits.

A further class of oligonucleotide mimetic that can be used for nucleic acid capture probes in several embodiments is cyclohexene nucleic acids (CeNA). In CeNA oligonucleotides, the furanose ring normally present in a DNA or RNA molecule is replaced with a cyclohexenyl ring. CeNA DMT protected phosphor amidite monomers have been prepared and used for oligomeric compound synthesis following classical phosphor amidite chemistry. Fully modified CeNA oligomeric compounds and oligonucleotides having specific positions modified with CeNA have been prepared and studied (Wang et al., J. Am. Chem. Soc, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes.

In several embodiments, a nucleic acid capture probe can comprise a locked nucleic acid (LNA), which can increase the sensitivity and specificity of conventional oligonucleotides, such as DNA oligonucleotides, for hybridization to short target sequences such as mature miRNAs, stem-loop precursor miRNAs, pre-miRNAs, siRNAs or other non-coding RNAs as well as miRNA binding sites in their cognate mRNA targets, mRNAs, mRNA splice variants, RNA-edited mRNAs, antisense RNAs and small nucleolar RNAs (snRNA).

Locked nucleic acid (LNA) capture probes are nucleoside or nucleotide analogues that include at least one LNA monomer (e.g., an LNA nucleoside or LNA nucleotide). LNA monomers are described in, for example, WO 99/14226, U.S. Pat. No. 6,043,060, U.S. Pat. No. 6,268,490, WO 01/07455, WO 01/00641, WO 98/39352, WO 00/56746, WO 00/56748 and WO 00/66604. LNAs have bicyclic sugar moieties "in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol, 2001, 8 1-7; and Oram et al., Curr. Opinion Mol. Ther., 2001, 3, 239-243; see also U.S. Pat. Nos. 6,268,490 and 6,670,461). The synthesis and preparation of the LNA monomers adenine, cytosine, guanine, 5-methylcytosine, thymine and uracil, along with their oligomerization, and nucleic acid recognition properties have been described (Koshkin et al., Tetrahedron, 1998, 54, 3607-3630).

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

In several embodiments, a nucleic acid capture probe can include a non-native, degenerate, or universal base such as inosine, xathanine, hypoxathanine, isocytosine, isoguanine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine, or the like. In some embodiments, a nucleic acid capture probe can include isocytosine and/or isoguanine in order to reduce non-specific hybridization as generally described in U.S. Pat. No. 5,681,702.

In several embodiments, a nucleic acid capture probe can comprise an "aptamer" to bind to a nucleic acid or polypeptide analyte of interest. Aptamers are described in U.S. Pat. Nos. 5,270,163; 5,475,096; 5,567,588; 5,595,877; 5,637,459; 5,683,867; and 5,705,337; which are herein incorporated by reference in their entireties. Aptamers can bind to various molecular targets such as small molecules, proteins, and nucleic acids.

In several embodiments, the particle associated with the nucleic acid capture probe comprises a nanoparticle, nanosphere, microcapsule, nanocapsule, microsphere, microparticle, bead, colloid, aggregate, flocculate, insoluble salt, emulsion, crystal, detergent, surfactant, dendrimer, copolymer, block polymer, nucleic acid, carbohydrate, lipid, liposome, or insoluble complex. It is contemplated that these types of particles can have any size in the picometer, nanometer, micrometer, or millimeter range along any dimensional axis. As used herein, the term "nanoparticle" refers to any particle having a greatest dimension (e.g., diameter) that is less than about 2500 nm. In some embodiments, the nanoparticle is a solid or a semi-solid. In some embodiments, the nanoparticle is generally centrosymmetric. In some embodiments, the nanoparticle contains a generally uniform dispersion of solid components.

Nanoparticles can have a characteristic dimension of less than about 1 micrometer, where the characteristic dimension of a particle is the diameter of a perfect sphere having the same volume as the particle. For example, the nanoparticle may have a characteristic dimension that is less than 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm, or 20 nm, or any number in between the aforementioned sizes. In some embodiments, the nanoparticle can have a characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm or 300 nm, or any number in between the aforementioned sizes. In other embodiments, the nanoparticle can have a characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm or 200-300 nm.

In several embodiments, a particle comprises a metal particle, such as an Au, Ag, Pd, Pt, Cu, Ni, Co, Fe (e.g. iron sulfide), Mn, Ru, Rh, Os, or Ir particle. In various embodiments, a particle comprises a metal oxide particle. Examples of suitable metal oxide particles include zinc oxide, titanium (di)oxide, iron oxide, silver oxide, copper oxide, aluminum oxide, or silicon (di)oxide particles. In certain embodiments, a particle comprises a magnetic particle, such as a magnetic bead, nanoparticle, microparticle, and the like.

Where the analyte of interest is a nucleic acid molecule, several embodiments relate to methods of detecting a nucleic acid molecule of interest in a sample comprising: providing a hMRS comprising a nucleic acid capture probe associated with a magnetic responsive nanoparticle, wherein the capture probe is capable of hybridizing to the nucleic acid molecule of interest to form a duplex; applying a sample for which the presence or absence of the nucleic acid molecule of interest is to be determined to the hMRS under conditions in which the nucleic acid molecule of interest, when present, and the capture probe sequence—specifically hybridize to form a duplex; and determining the presence or absence of the nucleic acid molecule of interest by detecting an alteration in a magnetic property of the hMRS or sample. In a specific example, the alteration in a magnetic property is a change in the magnetic resonance signal of the hMRS or the environment surrounding the hMRS. A change in the magnetic resonance signal can include an increase or decrease in the T2 of the hMRS and/or sample. This can be further defined in relation to a negative control. In some aspects, the concentration of the nucleic acid analyte of interest in the sample is measured. Detecting and/or measuring the concentration of a nucleic acid molecule of interest in a sample can be done in real-time and/or in multiplex with other analytes of interest or samples.

Typically, the target analyte is isolated before being subjected to hMRS. The terms "isolate", "isolated" or "isolation" when used with respect to the target analyte, e.g., nucleic acid analyte, means enriching the target analyte relative to its natural environment. Thus, enrichment could include partial purification or full purification, but in most cases simply means removing components from the crude sample. In the case of a blood sample, isolation might include a centrifugation step and removing a portion of the centrifuged sample.

There are varieties of ways that the nanoparticles can be prepared, but typically, the result involves a nanoparticle with functional groups that can be used to associate the nanoparticle to the binding moiety. The terms "association", "associating" or "associate" with respect to the interaction between the nucleic acid capture probe and the particle generally refers to the adherence interaction (typically covalent binding) that is direct, such as directly to the material of which the particle is composed, or indirect, such as interaction with a coating (e.g. polymer coating) on the particle. Typically, association of the nucleic acid can be associated through non-polymer surface functionalization of the particle or via functionalized polymers on the particle. According to one embodiment, the hMRS is a nanoparticle that is composed of a magnetic metal oxide and includes one or more functional groups, e.g., a polymer comprising one or more functional groups. When polymers are included, they contain functional groups that enable the nucleic acid to be attached to the nanoparticle to form the conjugate. The polymer can be a natural polymer, a synthetic polymer, a combination of natural and synthetic polymers, or derivatives of each type. The functional groups can be carboxy, amino, or sulfhydryl groups. In some embodiments, the binding moiety is attached to the nanoparticle through disulfide groups. The metal oxides can also be associated with non-polymer functional groups to form the nanoparticles.

In one example, nucleic acids can be linked to the metal oxide through covalent attachment to a functionalized polymer or to non-polymeric surface-functionalized metal oxides. In the latter method, the nanoparticles can be synthesized according to the method of Albrecht et al., Biochimie, 80 (5-6): 379-90, 1998. Dimercapto-succinic acid is coupled to the iron oxide and provides a carboxyl functional group. By functionalized is meant the presence of amino or carboxyl or other reactive groups.

In another example, oligonucleotides are attached to magnetic nanoparticles via a functionalized polymer associated with the metal oxide. In some embodiments, the polymer is hydrophilic. In a specific embodiment, the conjugates are made using oligonucleotides that have terminal amino, sulfhydryl, or phosphate groups, and superparamagnetic iron oxide nanoparticles bearing amino or carboxy groups on a hydrophilic polymer. There are several methods for synthesizing carboxy and amino derivatized-nanoparticles. Methods for synthesizing functionalized, coated nanoparticles are discussed in further detail below.

Carboxy functionalized nanoparticles can be made, for example, according to the method of Gorman (see WO 00/61191). In this method, reduced carboxymethyl (CM) dextran is synthesized from commercial dextran. The CM-dextran and iron salts are mixed together and are then neutralized with ammonium hydroxide. The resulting carboxy functionalized nanoparticles can be used for coupling amino functionalized nucleic acids.

Carboxy-functionalized nanoparticles can also be made from polysaccharide coated nanoparticles by reaction with bromo or chloroacetic acid in strong base to attach carboxyl groups. In addition, carboxy-functionalized particles can be made from amino-functionalized nanoparticles by converting amino to carboxy groups by the use of reagents such as succinic anhydride or maleic anhydride.

Nanoparticles can also be synthesized according to the method of Molday (Molday, R. S, and D. MacKenzie, "*Immunospecific ferromagnetic iron-dextran reagents for the labeling and magnetic separation of cells*," J. Immunol. Methods, 1982, 52(3):353-67, and treated with periodate to form aldehyde groups. The aldehyde-containing nanoparticles can then be reacted with a diamine (e.g., ethylene diamine or hexanediamine), which will form a Schiff base, followed by reduction with sodium borohydride or sodium cyanoborohydride.

Dextran-coated nanoparticles can be made and cross-linked with epichlorohydrin. The addition of ammonia will react with epoxy groups to generate amine groups, see Hogemann, D., et al., *Improvement of MRI probes to allow efficient detection of gene expression* Bioconjug. Chem. 2000. 11(6): 941-6, and Josephson et al., "*High-efficiency intracellular magnetic labeling with novel superparamagnetic-Tat peptide conjugates*," Bioconjug. Chem., 1999, 10(2):186-91. This material is known as cross-linked iron oxide or "CLIO" and when functionalized with amine is referred to as amine-CLIO or $NH_2$-CLIO.

Carboxy-functionalized nanoparticles can be converted to amino-functionalized magnetic particles by the use of water-soluble carbodiimides and diamines such as ethylene diamine or hexane diamine.

Avidin or streptavidin can be attached to nanoparticles for use with a biotinylated binding moiety, such as an nucleic acid. See e.g., Shen et al., "*Magnetically labeled secretin retains receptor affinity to pancreas acinar cells*," Bioconjug. Chem., 1996, 7(3):311-6. Similarly, biotin can be attached to a nanoparticle for use with an avidin-labeled binding moiety.

Another example of a polymer coating for the particle is a polyacrylic acid. The method of producing these is described further in the Examples section.

According to an alternative embodiment, provided is a method to detect for the presence of antibodies in a biological sample. The method may include contacting the sample with a nanosensor that includes a nanoparticle associated with a binding molecule (such as a polypeptide) having an epitope to an antibody of interest. The term "polypeptide" as used herein pertains to two or more linked amino acids, and would include proteins. For example, if an antibody of interest is present in the sample, it would bind to the epitope containing polypeptide which would modulate the resonance signal of the sample and/or nanosensor. The polypeptide could pertain to a protein specific to a certain microorganism (such as MAP protein). If a subject has been exposed to a certain microorganism, the subject will most likely generate antibodies against that organism. Thus, if a change magnetic resonance signal is detected, then this indicates that the subject has been exposed. This type of assay is analogous to the classic TB skin test. However, instead of detect an immune reaction on the skin due to the presence of antibodies, the antibody-specific nanosensors will detect the presence of antibodies in a sample through observed changes in a magnetic response.

According to a related embodiment, provided is an antibody-specific nanosensor. The antibody-specific nanosensor includes a magnetically responsive nanoparticle associated with a molecule having an epitope to an antibody of interest. In a specific embodiment, the molecule having an epitope to an antibody of interest is a polypeptide.

Examples

Design and Synthesis of hMRS

Figure 7:
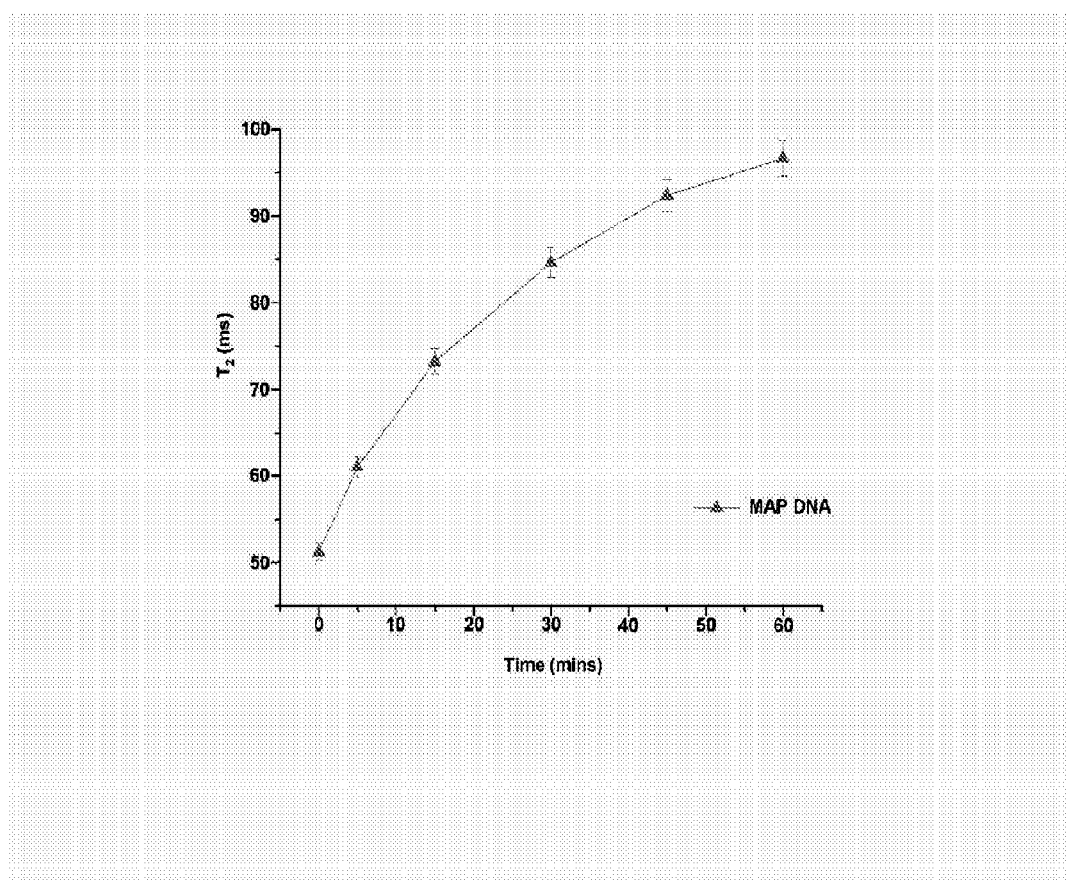
FIG. 7 Kinetics for MAP's IS900 genomic marker detection with hMRS. After heating the samples to facilitate DNA stand separation and hMRS hybridization, the changes in the $T_2$ magnetic resonance signal were recorded over time, with marked changes occurring within less than an hour (Means±SE).

The detection of MAP's 15900 genomic marker relies on DNA isolation and subsequent amplification and detection via PCR. Typically, DNA from peripheral leukocytes found in the buffy coat (Direct nPCR) or leukocyte-derived cultured bacteria (Culture-based nPCR) is first isolated in a multistep protocol [21], yielding bacterial DNA of high quality (FIG. 1a). However, this approach often times compromises DNA yield, which may impede MAP identification. In subsequent steps, the bacterial DNA is subjected to two 3-hour-long polymerase-mediated amplification rounds of the IS900 locus, followed by gel electrophoresis. To facilitate faster detection via magnetic relaxation, a single hMRS probe was designed that hybridizes with the unique IS900 sequence within the MAP plasmid. These hMRS are composed of a polyacrylic acid-coated iron oxide nanoparticle onto which an oligonucleotide sequence (ATGTGGTTGCTGTGT (SEQ ID NO. 1)) complementary to the IS900 sequence in MAP is conjugated to facilitate binding and detection. The resulting MAP specific hMRS had a diameter of 78±3 nm, zeta potential value of −35 mV, an average of 55 oligonucleotides per nanoparticle, with R1 and R2 relaxivities (at 0.47T) of 45 mM−1s−1 and 60 mM−1s−1 respectively. We anticipated that hMRS could utilize crude DNA, obtained from isolated buffy coats that have been subjected to heating (FIG. 1a). It is well reported that heating of peripheral leukocytes accomplishes first the release of a pathogen from intracellular compartments [21], such as phagosomes, due to extensive pore formation on the host cell's plasma membrane and organelles' phospholipid-containing membrane. Once exposed to high temperatures, the pathogen's structural integrity is affected, leading to release of its genomic DNA to the aqueous milieu. A series of heating and cooling procedures on the isolated MAP DNA plasmid in the presence of hMRS reduces the DNA torsional strain, facilitating annealing and hybridization of the hMRS onto the IS900 region of the MAP genome (FIG. 1b). Decreasing the sample's temperature can return the DNA to a higher structural order, with the hMRS still binding to the MAP genome and inducing increases in the sample's magnetic resonance signal. Specifically, the hMRS were able to bind to MAP DNA after two short heating rounds (3 min each at 95° C.), followed by unassisted cooling to room temperature. The fast changes in the magnetic resonance signal were monitored with a compact nuclear magnetic resonance instrument (0.47T, Bruker, Minispec), recording increases in the sample's transverse relaxation times ($\Delta T2+$, where T2(sample)>T2(control)). Within 30 minutes after removing the samples from heat, significant and reproducible changes were observed prompting us to set this time-point as the hMRS readout point (FIG. 7). Based on the observation that the sample's T2 times were higher than those of the sterile control throughout the experimental time course, it was deduced that the hMRS first bound to the relaxed circular MAP DNA that was heated, while the hMRS still remained bound to the cooled DNA as it was returning to its supercoil form. These results were corroborated by dynamic light scattering studies that showed no clustering of the nanoparticle suspension upon addition of the isolated MAP genome, since the nanoparticle diameter was found to be 81±5 nm. Likely, this may be attributed to the fact that during sample cooling the DNA returned to its supercoiled conformation, which can be in the order of a few nanometers, and as a result nominally altering the overall size of the hybridizing nanoparticle-DNA complex.

hMRS are Specific and Sensitive Probes

Specificity is a critical component of any assay, supporting correct diagnosis and therapeutic intervention. To determine the specificity of the hMRS, we incubated the hMRS (6 µg Fe/mL) with pure DNA extracts from various mycobacteria and monitored changes in T2 signal.

Figure 2:
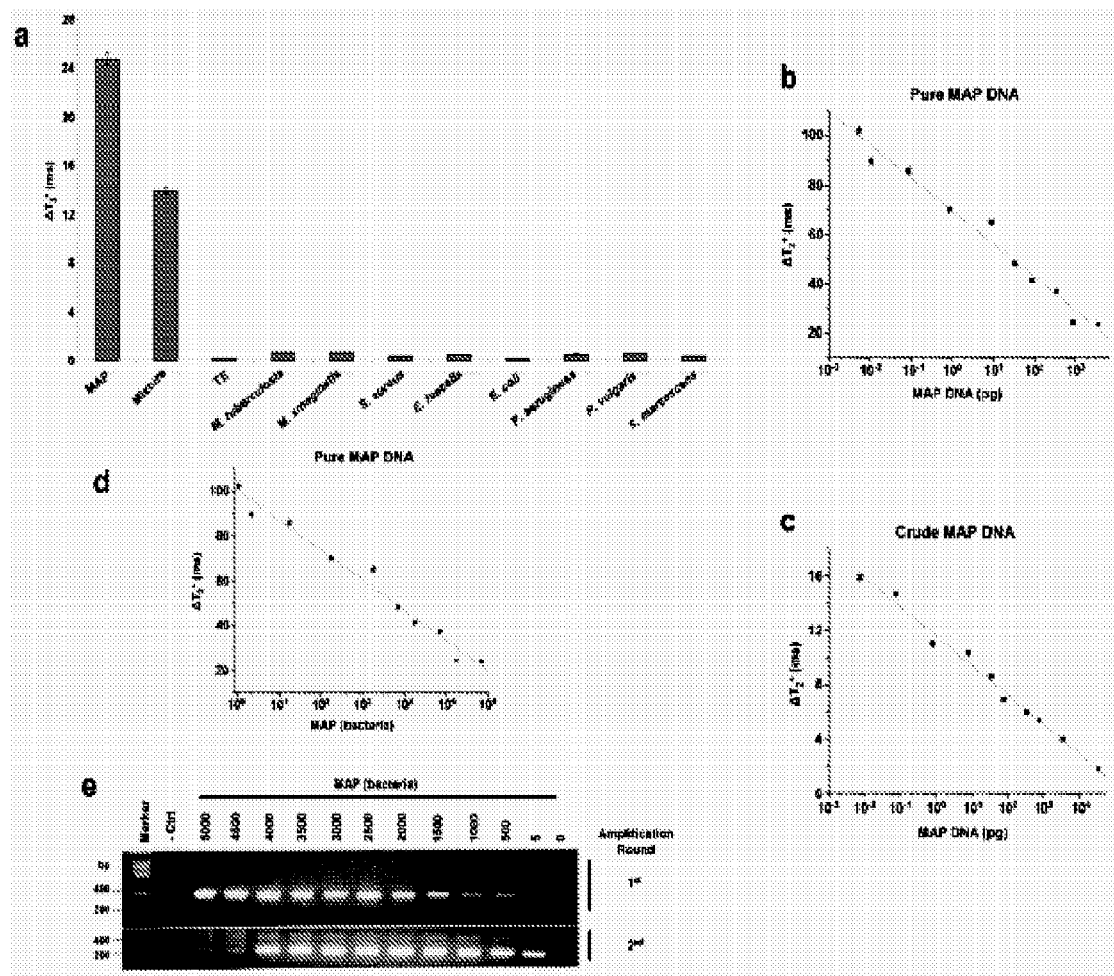
FIG. 2 Specificity and sensitivity of the IS900-detecting hMRS. (a) hMRS specifically bind to MAP DNA and not DNA from other mycobacteria or common pathogens ([hMRS]=3 μg Fe/μL). hMRS facilitates the fast and quantitative detection of MAP DNA in pure (b) and crude (c) samples within 30 minutes. Comparison of the sensitivity of the hMRS and nested PCR (nPCR). (d) Within 30 minutes, the hMRS detected a single MAP genome copy, translating to one bacterium. (e) After its second amplification round (6 hours), nPCR achieved comparable sensitivity. (Upper gel image: first nPCR round (3 hours), lower gel image: second nPCR round (total two-round time 6 hours), –Ctrl: dH₂O and 0: sterile TE buffer).

Within 30 minutes, results indicated that only samples containing MAP DNA exhibited a high $\Delta T2+$ signal, being attributed to the hMRS-MAP DNA binding (FIG. 2a). Additionally, the hMRS were still able to identify their target in a solution with a mixture of MAP and other mycobacterial DNA (FIG. 2a). This indicates that the hMRS are sensitive and specific, without being affected by the presence of other mycobacterial DNA. Furthermore, addition of a synthetic oligonucleotide complementary to the IS900 sequence abrogated the signal of the hMRS upon MAP DNA addition, confirming the specificity of the hMRS probe (data not shown). Since other microorganisms' DNA might be found in a clinical sample, we examined if the hMRS could differentiate between MAP and common Gram positive and Gram negative bacteria, as well as different types of mycobacteria. Results showed that only the MAP sample yielded a high $\Delta T2+$, whereas the other bacterial DNA samples exhibited signal proximal to that of the sterile control (FIG. 2a). These data hint the potential use of the hMRS and magnetic relaxation detection for the fast and specific detection of MAP DNA.

Figure 3:
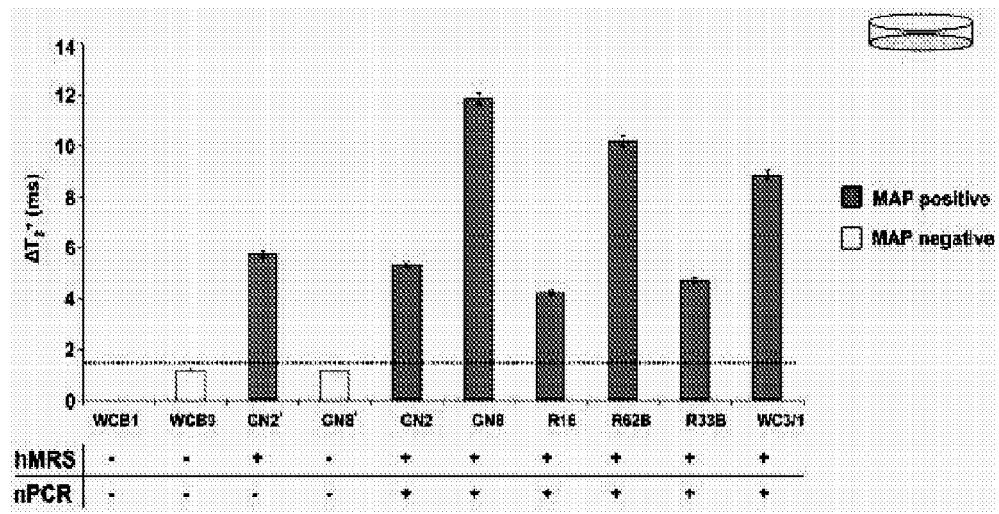
FIG. 3 Screening of clinical isolates with hMRS and nPCR. Comparison between the magnetic relaxation-mediated detection of MAP in clinical isolates using hMRS after crude DNA extraction and culture-based nPCR. All isolates were from blood samples from Crohn's disease patients, apart from GN2' and GN8' that correspond to ileal biopsies.
Figure 8:
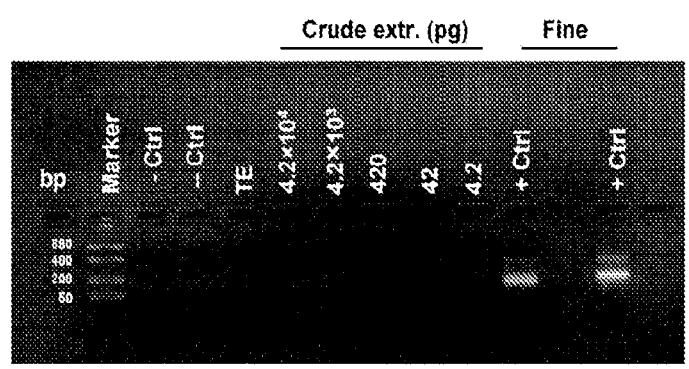
FIG. 8 Nested PCR (nPCR) cannot quantify crude MAP DNA. –Ctrl: negative control (dH2O) of the first nPCR round, –Ctrl: negative control (dH2O) of the second nPCR round, TE: TE buffer, +Ctrl: two controls of pure extracted MAP DNA.
Figure 9:
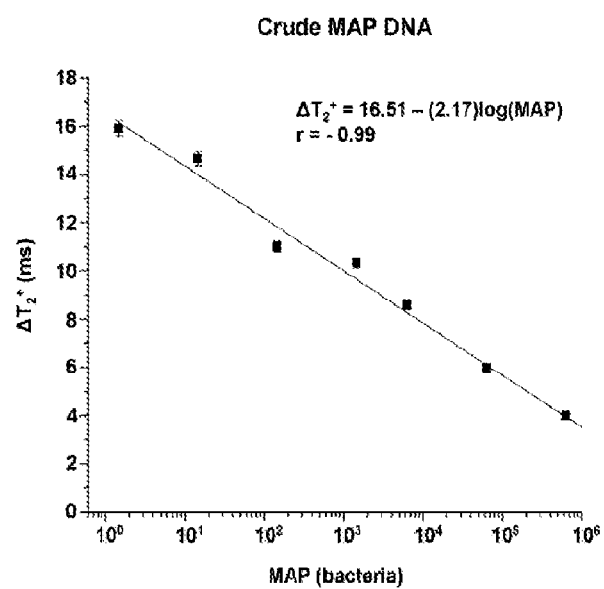
FIG. 9 Genome-copy-based quantification of MAP with hMRS and crude extracted DNA. Samples with known amounts of crude DNA from cultured MAP were utilized to correlate the changes in the T2 signal ($\Delta T2+$) and the number of bacteria originally present in the sample, using the MAP's genome size as a reference. (Means±SE. SE too small to depict in high bacterial levels.)

In subsequent studies, whether the hMRS could quantify MAP DNA was determined. MAP DNA was isolated using either an elaborate multistep extraction protocol to obtain pure DNA, or a fast 30-minute boiling-based methodology to obtain crude DNA. After a 30-minute incubation period, the hMRS were able to detect MAP DNA in both pure and crude DNA preparations, exhibiting concentration-dependent $\Delta T2+$ changes (FIGS. 2b and 2c, Table S1). The observed MAP concentration response pattern exhibited a high magnetic resonance signal ($\Delta T2+$) at low target concentration levels and low signals at higher DNA concentrations. This suggests that the binding between the hMRS and MAP DNA was facilitated via low valency interaction, as previously described in other models [11]. This unique interaction mechanism provides enhanced sensitivity during the screening of scarce biomarkers, since high signal is desired at low target concentrations. Quantification of the number of oligonucleotides on the hMRS probe revealed that on average there were 55 oligonucleotides (oligos) per hMRS. This level of oligos per nanoparticle is in line with previous reports, where valency grafting of 46 oligos per nanoparticle exhibited a low valency binding behavior, whereas a nanoparticle with 368 oligos obeyed a high valency mechanism [12]. A low-valency-based detection approach is ideal for the identification of MAP in clinical samples, since it will induce a prominent $\Delta T2+$ signal at low numbers of MAP. Based on the findings that both pure and crude MAP DNA exhibited similar hMRS quantification patterns, it was deduced that the hMRS assay can detect IS900 independent of the sample's DNA extraction methodology. Although higher changes were recorded in pure MAP DNA samples, both extraction methodologies had equivalent detection thresholds, reaching low femtogram (10-15) levels. Potentially the differences in the magnitude of the $\Delta T2+$ from pure and crude MAP DNA might be attributed to the sample's unique characteristics. It is plausible that the high purity of the pure DNA extracts is associated with marginal protein and lipid levels, resulting in lower viscosity. Alternatively, a crude MAP DNA sample may have substantially higher content of proteins and lipids, thus higher viscosity, which may be reflected in lower $\Delta T2+$ values upon IS9000-hMRS hybridization. We then examined whether nested PCR (nPCR) can achieve comparable sensitivity using crude MAP DNA. We decided to compare our hMRS method with nPCR as opposed to reverse transcriptase PCR (RT-PCR), due to the fact that MAP is an intracellular pathogen that grows very slowly. Similar to other intracellular microorganisms, it can be dormant and reduce its metabolism, suppressing transcriptional and translational activity [21]. As a result, the transcripts (mRNA) of even housekeeping genes are nominal and cannot be used in RT-PCR diagnostics. Therefore, nPCR is the technique most typically used for MAP detection [21]. Using nPCR, after two 3-hour-long cycles and electrophoresis, nPCR was not able to detect MAP IS900 in samples containing crude MAP DNA (FIG. 8). This demonstrates the sensitivity and robustness of hMRS to rapidly detect their target even under conditions of interference, which prevent the use of traditional enzyme-based methods. In line with this, recent studies have demonstrated that nucleic-acid-decorated nanostructures can be highly stable even in serum-containing media and avoid non-specific protein and nuclease interactions, due to the steric inaccessibility and high local salt concentration introduced by the nanoparticles' DNA strands [26]. Subsequently, we then compared hMRS and nPCR using purified DNA extracts instead. Also considering the size of MAP's genome (4,829,781 bp) and the average molecular weight of a base pair (MW: 650), we calculated the mass of a single MAP genome copy to be equal to 5.2 fg. This value is comparable to that determined experimentally in previous reports [27]. Hence, we accordingly prepared serial dilutions of MAP DNA with known genome copy numbers. hMRS and magnetic relaxation detection were able to detect a single copy of MAP DNA within 30 minutes, whereas nPCR was able to achieve similar, although not as sensitive, detection (5 bacteria) only after the second amplification round (FIGS. 2d and 2e, Table S2). This translates to a total readout time for nPCR of more than 6 hours, with the need of more reagents, such as primers and enzymes, as well as labor and equipment time. Intriguingly though, the hMRS had a single genome-copy detection threshold when crude MAP DNA was used, without compromising their sensitivity in this minimally processed sample (FIG. 9). Overall, these data demonstrate that hMRS can achieve fast single MAP genome detection even in crude DNA samples, outperforming nPCR in readout time, sensitivity and robustness.

hMRS Achieve Genome-Based Detection of the Intracellular Pathogen *Mycobacterium avium* Spp. *Paratuberculosis* in Cultured Clinical Isolates and Tissue Samples Since the hMRS detected MAP DNA in samples from pure bacterial cultures, we investigated if the nanosensors could identify their targets in more complex samples, such as cultured clinical isolates and homogenized tissue preparations. We first screened cultures of clinical isolates from Crohn's disease patients with the hMRS and compared these results with nPCR. Specifically, we used crude DNA for the hMRS and pure DNA for the nPCR, since nPCR cannot utilize crude DNA. Following a single-step procedure, crude DNA obtained from cultured isolates of healthy individuals yielded a magnetic signal change that was comparable to that of the sterile culture medium ($\Delta T2+=1.3\pm0.2$ ms), establishing this magnetic signal change as the hMRS negative control baseline. Further studies indicated that the hMRS were able to rapidly detect MAP in several clinical isolates with good correlation to the culture-based nPCR, indicating that the hMRS can quickly detect the IS900 biomarker in minimally processed cultured clinical isolates (FIG. 3, Table S3). Out of the ten cultures screened, one sample from a culture of an ileal biopsy (GN2') was identified as positive by the hMRS, yet negative by nPCR. A false negative result with culturing methods can occur when either low amounts of the pathogen are present in the collected sample or when the pathogen is not viable to properly grow in culture. This prompted us to analyze the culture sample from the corresponding patient's blood (GN2). We reasoned that viable MAP could be present in the patient's leukocytes, granting correct diagnosis. Indeed, culture from the blood sample GN2 was identified as positive in agreement with the hMRS diagnosis and clinical symptomology. Therefore, nPCR may have failed to detect IS900 in ileal biopsy GN2' perhaps due to either low levels of the pathogen or the presence of interferences in the biopsy sample that inhibited growth of the pathogen in culture. Overall, these results suggest that the high sensitivity of hMRS facilitates the positive identification of MAP in blood and biopsy samples, whereas PCR techniques were not always successful in identifying MAP.

Figure 4:
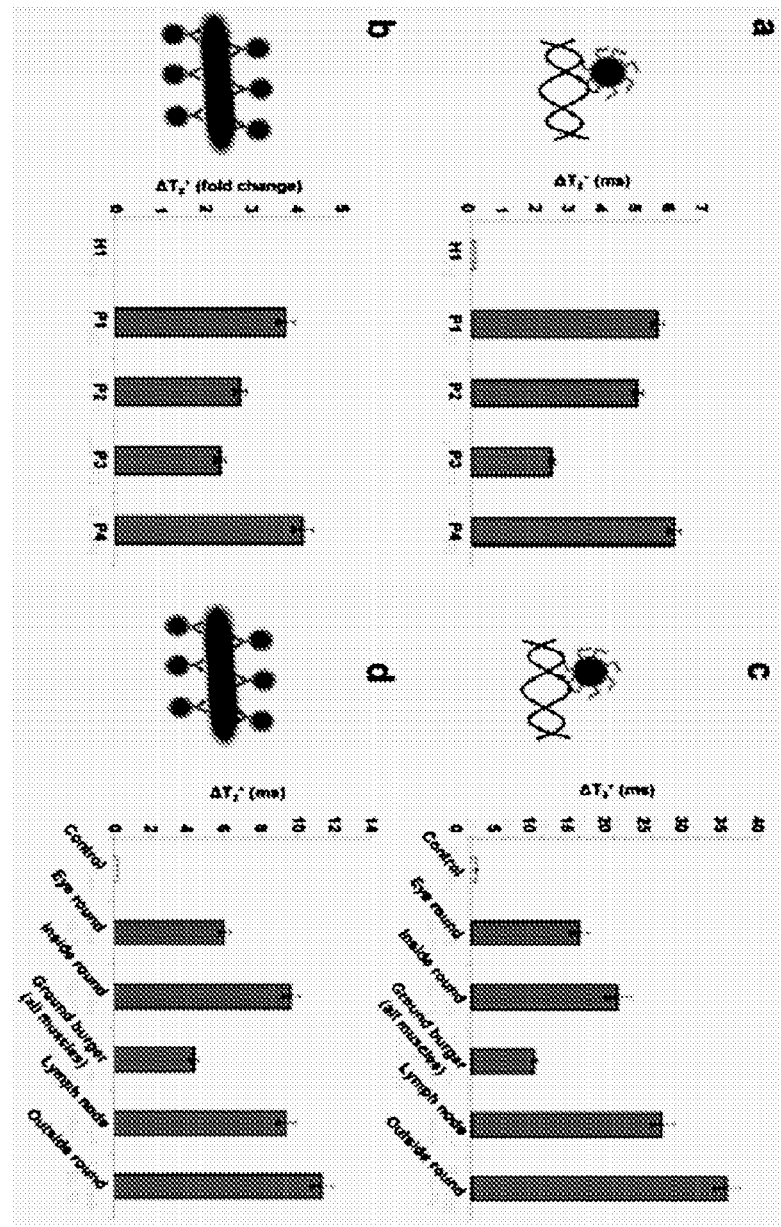
FIG. 4 Comparison between the hMRS genomic detection of MAP in clinical isolates and homogenized tissues with the presence of MAP protein markers using anti-MAP antibodies conjugated MRS. (a) hMRS detected MAP genomic tags in clinical isolates via changes in the magnetic resonance signal. (b) A second preparation of magnetic nanosensors carrying polyclonal anti-MAP antibodies (anti-MAP-pAb) was able to corroborate the presence of MAP in these clinical isolates by the identification of MAP surface epitopes. (c) hMRS detected MAP's IS900 in homogenized tissue from Johne's disease cattle. (d) Corroboration of the presence of MAP in the cattle samples using anti-MAP-pAb MRS nanosensors.

Next, we screened various ileal biopsies from Crohn's disease patients for the presence of MAP at the genomic and epitope levels using magnetic relaxation. We performed these studies since clinical diagnostics frequently require the identification of a biomarker at multiple levels. For instance, the aberrant activity of an oncogene has to be evaluated at the transcriptional, translational and post-translational levels, in order to understand causality, delineate disease dynamics and identify optimal therapy [28], [29], [30]. For these studies, in addition to the MAP IS900 hybridizing sensor (hMRS), we prepared a MAP-epitope-sensing MRS (diameter=92±4 nm, zeta potential=−31 mV, an average of 2 antibodies per nanoparticle, R1=48 mM−1s−1 and R2=57 mM−1s−1) that identifies a conserved MAP bacterial surface antigen [31]. Despite their different detecting mechanisms (oligonucleotide probe vs antibody), binding site topology and target characteristics (DNA vs surface epitope), both MRS provided a $\Delta T2+$ signal for all samples with clinical symptomology (P1-P4, FIGS. 4a and 4b), whereas the sample from a healthy individual (H1, FIGS. 4a and 4b), exhibited nominal magnetic signal changes. Independent confirmation of the MAP MRS findings was achieved by performing DNA extraction and nPCR analysis. In addition, we used both the hMRS and epitope MRS to screen for the presence of MAP in tissue samples from cattle infected with Johne's disease. Since MAP causes Johne's disease in cattle, we investigated if these probes can identify this intracellular pathogen at the genomic and epitope levels in homogenized tissue samples. Results showed significant magnetic signal changes in all tissues from infected animals (FIGS. 4c and 4d), demonstrating that hMRS and epitope MRS can quickly detect MAP in clinically relevant samples at both the genomic and epitope levels. It is interesting to note that in both human biopsies from Crohn's patients and tissues from animals with Johne's disease, the magnetic relaxation signal obtained with the hMRS probe correlates with that obtained with the epitope-sensing MRS for the same sample. The differences in the $\Delta T2+$ among the animal tissue samples might be attributed to the fact that the spatial concentration of MAP differs among the various tissues within the same animal due to Johne's disease pathophysiology. Overall, these results indicate that these probes can be used for the screening of complex tissue samples with minimal or no sample preparation, supporting clinical decision making.

hMRS Quickly Detect MAP DNA in Peripheral Blood

Figure 5:
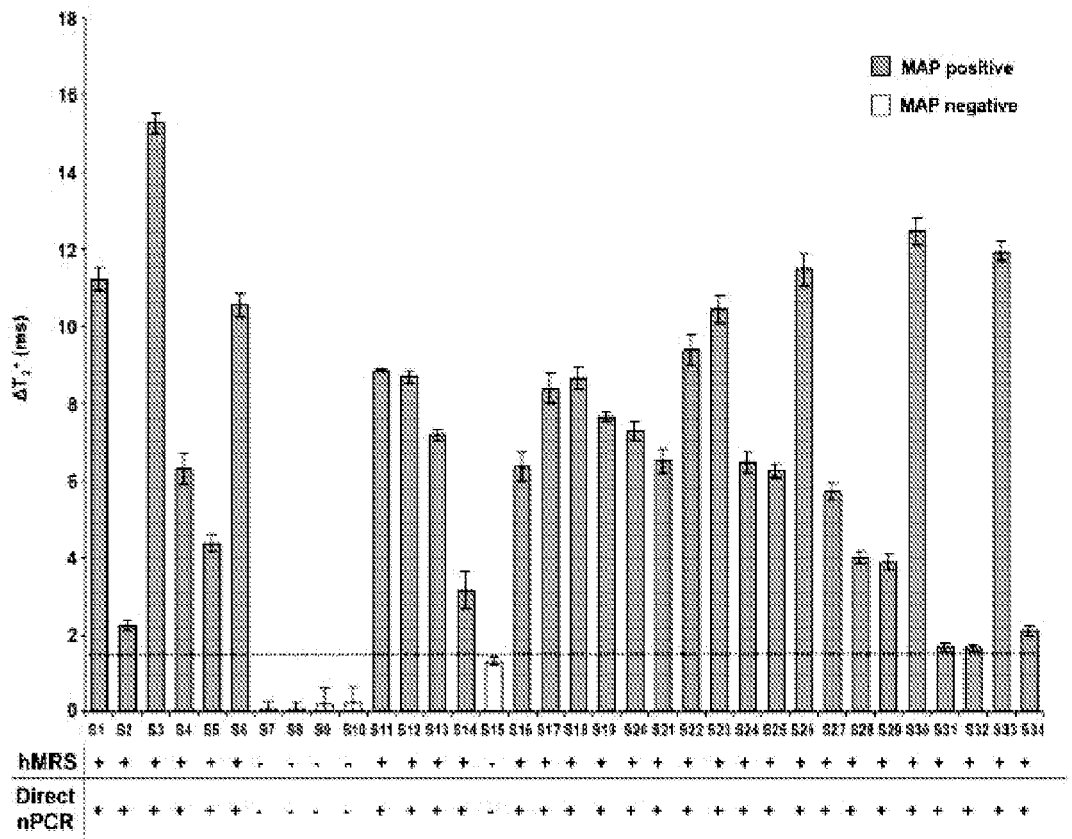
FIG. 5 Detection of *Mycobacterium avium* spp *paratuberculosis*' genomic marker in clinical samples with hMRS and direct nPCR. The hMRS detected MAP's IS900 region in minimally processed blood samples (Cohort 1, n=34). Correlation of the hMRS findings was achieved through pure DNA extraction from white blood cells and direct nPCR. Results are means±SE.

Acknowledging previous reports that identified MAP in the blood of Crohn's disease patients, we sought to screen blood samples from healthy individuals and Crohn's disease patients for the presence of IS900 (n=34). For this, we chose to screen MAP's IS900 genomic marker, rather than a protein (epitope) marker, since the later involves the use of anti-MAP antibodies that are difficult to reproducibly generate while avoiding antibody batch variabilities. In addition, a DNA-based hybridizing MRS would be more robust and selective than an antibody-based MRS. Peripheral blood was collected and DNA was directly isolated from white blood cells, via either a 30-minutes crude DNA extraction protocol for hMRS or a multistep high purity and quality DNA isolation procedure for direct nPCR screening. Direct nPCR for the MAP IS900 biomarker provided conclusive results about the pathogen's presence in these samples, hence these samples established the first peripheral blood cohort (Cohort 1). In this cohort, positive samples were defined as those samples where a prominent band corresponding to IS900 was observed and negative samples were those where no visible band was observed at all. Control and Cohort 1 samples were screened with hMRS, after a 30-minutes crude DNA extraction protocol from white blood cells. Crude DNA extracted from control samples induced small changes in the magnetic signal ($\Delta T2+=1.3\pm0.1$ ms), which served as the hMRS reference point. Interestingly, results obtained with hMRS and magnetic relaxation detection using crude DNA samples from patients within Cohort 1 were in complete agreement with results obtained with direct nPCR that used pure DNA samples (FIG. 5, Table S4). Addition of a synthetic target complementary to hMRS led to signal abrogation in the samples that had been identified as MAP positive, confirming the specificity of the assay. This indicates that the hMRS can detect their target in minimally processed blood samples, while eliminating lengthy sample preparation procedures.

Next, a second cohort of blood samples (Cohort 2, Table 1) was represented by samples where direct nPCR analysis provided dubious results. In samples within this cohort, classification as either positive or negative was not possible due to the presence of smeared or faint bands. The presence of these dubious samples, either false-positives or false-negatives, is a major problem with current nPCR techniques. Therefore, we examined if the hMRS performs better than direct nPCR and culture-based nPCR in determining if an individual is positive or negative based on his/her clinical state (in this case being Crohn's positive or healthy). For the culture-based nPCR, inoculants from white blood cells were incubated for 12 weeks in specialized mycobacterial media (n=26), allowing the potential growth of any viable MAP bacteria. After this long incubation period, pure DNA extraction was performed, followed by nPCR analysis. Interestingly, the culture-based nPCR was better in predicting disease than direct nPCR, which was performed on pure DNA extracted from white blood cells readily after venipuncture (blood draw) (FIGS. 6a and 6b). This may be attributed to the ability of bacterial culturing to provide more high-quality MAP DNA, as opposed to DNA directly obtained from white blood cells. Additionally, it is plausible that culturing can facilitate growth of even low populations of bacteria in optimal conditions, whereas direct pure DNA isolation from white blood cells may result in low genome recoveries of rare bacteria throughout its multiple steps and presence of interferences, like nucleases, cytosolic proteins and membrane lipids. Comparing both PCR setups with the crude DNA hMRS methodology, we found that the nanoparticle-based method outperformed both PCR-based methods in correlating MAP's presence and disease state (FIGS. 6a and 6b). This hints the hMRS' sensitivity, and the ability of the crude DNA extraction method to provide adequate DNA levels that are sufficient to facilitate improved bacterial detection. Furthermore, a receiver operating characteristic (ROC) analysis based on hMRS-mediated MAP quantification indicated that hMRS can provide improved clinical diagnosis than the qualitative (positive vs negative) nested PCR assays (FIG. 6a, Table 1). Specifically, hMRS were able to better correlate bacterial biomarker presence and Crohn's disease symptomology than both direct and culture-based nPCR. This suggests the potential use of hMRS for the future investigation of complex disease and the role of various disease effectors and contributors, to better understand pathogenesis' mechanisms and its dynamic interactions. Taken together, this data prove that hMRS can rapidly detect a unique nucleic acid signature of an intracellular pathogen in clinical samples with improved fidelity and higher sensitivity than PCR. This enhanced detection translates into a more sensitive pathogen detection and more accurate diagnosis of the disease, providing important clinical information for successful treatment and therapeutic interventions due to early diagnosis.

TABLE 1

Clinical data and hMRS results of minimally processed blood samples (Cohort 2)

| Sample | Age (years)/sex | Diagnosis | Direct PCR | Culture-based PCR | hMRS MAP | hMRS ΔT2 (ms) | hMRS MAP (bacteria) |
|---|---|---|---|---|---|---|---|
| B1 | F/51 | CD | − | + | + (3/3) | 8.4 | 5348 |
| B2 | F/27 | CD | − | + | + (3/3) | 8.6 | 4609 |
| B3 | F/73 | Healthy | − | + | + (3/3) | 9.1 | 2542 |
| B4 | F/50 | CD | − | + | + (3/3) | 3.4 | 1088531 |
| B5 | M/56 | CD | − | + | + (3/3) | 7.6 | 12826 |
| B6 | F/57 | Healthy | − | + | + (3/3) | 4.2 | 465264 |
| B7 | M/28 | CD | − | + | + (3/3) | 7.5 | 13963 |
| B8 | F/31 | Healthy | − | + | + (3/3) | 7.0 | 24006 |
| B9 | M/18 | CD | − | + | + (3/3) | 10.3 | 760 |
| B10 | M/28 | CD | − | + | + (3/3) | 5.2 | 162513 |
| B11 | F/16 | CD | − | + | + (3/3) | 4.4 | 400959 |
| B12 | F/24 | Healthy | + | − | − (0/3) | 0.2 | 0 |
| B13 | F/61 | Healthy | + | − | − (0/3) | 0.4 | 0 |
| B14 | M/65 | Healthy | + | − | − (0/3) | 0.1 | 0 |
| B15 | F/62 | Healthy | + | − | − (0/3) | 0.1 | 0 |
| B16 | F/23 | CD | + | − | − (0/3) | 0.7 | 0 |
| B17 | F/48 | Healthy | + | − | − (0/3) | 0.6 | 0 |
| B18 | M/19 | CD | + | − | − (0/3) | 0.0 | 0 |
| B19 | F/26 | Healthy | + | − | − (0/3) | 0.4 | 0 |
| B20 | M/43 | CD | + | − | − (0/3) | 0.0 | 0 |
| B21 | F/50 | CD | + | − | − (0/3) | 0.1 | 0 |
| B22 | F/12 | Healthy | + | + | − (0/3) | 0.5 | 0 |
| B23 | M/57 | Healthy | + | + | − (0/3) | 0.0 | 0 |
| B24 | F/23 | Healthy | + | + | − (0/3) | 0.6 | 0 |
| B25 | M/61 | Healthy | + | + | − (0/3) | 0.2 | 0 |
| B26 | F/49 | Healthy | + | + | − (0/3) | 0.3 | 0 |

Discussion

One of the aims of the studies in this Example was to develop and test a nanoparticle-based assay for the sensitive detection of genomic bacterial biomarkers of an intracellular pathogen in clinical samples. Preliminary studies demonstrated that the hMRS can specifically detect a conserved genomic element (IS900) in MAP's genome, and not in other microorganisms. Through additional studies, it has been identified that the sensitivity of the nanosensors was equal to one genome copy even in minimally processed samples, allowing detection of MAP in clinical isolates, tissue homogenates and blood. Compared to nPCR, hMRS had improved performance and yielded faster results. Consequently, this translates to lower costs, since the magnetic nanosensors are fairly easy and cheap to manufacture in larger quantities, and the assay does not require multiple oligonucleotide primer pairs, expensive enzymes and nucleotides. Detection was performed using a simple table-top relaxometer that measured the increase in the water proton relaxation time (NMR signal) that occurred after the hMRS probes bound to their genomic target. The unprecedented detection limit of this technique is due to the build-in water relaxation amplification that results upon a single binding event. The T2 relaxation times of hundreds of thousands of water molecules surrounding the hMRS probes increase upon binding of a single probe to the target. This is also facilitated by the low valency of the hMRS probe that induces drastic changes at low concentration of the target, or in this case low copy numbers of the genomic target. This approach contrasts with previous magnetic relaxation approaches that rely on the use of two magnetic nanoparticle probes that hybridize to adjacent sequences on a DNA target, facilitating clustering of the nanoparticles with a corresponding decrease in the T2 relaxation times [32], [33]. Since our approach does not rely on nanoparticle clustering and only the binding of the nanoparticle is sufficient for detection, a faster, more sensitive magnetic relaxation assay that rivals PCR has been developed for the screening of an intracellular pathogen genomic marker.

Apart from a table-top relaxometer, portable magnetic relaxometers have been developed, suitable for point-of-care screening with hMRS [34].

hMRS can be used for the detection of diverse targets in complex media, including turbid and opaque clinical samples [11], [12]. Herein, our results demonstrate that the hMRS binding can achieve the unprecedented and fast detection of a single genome copy of an intracellular pathogen. This is critical for the identification of extremely virulent pathogens. As MAP is an intracellular pathogen similar to *M. tuberculosis*, its detection is difficult, due to the pathogen's residence within an infected leukocyte's organelles. Thus contemporary diagnostic methodologies rely on cell isolation, cell lysis and nucleic acid isolation, in order to yield high purity DNA. This renders MAP's detection problematic since the microorganism has to be isolated from highly complex samples, such as blood or severely inflamed tissue biopsies, before amplification and detection via PCR analysis. Apart from DNA quality, the quantity of MAP DNA can affect the outcome of PCR. For instance, low MAP DNA levels from a clinical sample may not be successfully amplified through direct nPCR or biological matrix components can affect the polymerase activity, yielding false-negative or dubious results. In our studies, a significant number of samples that were identified as MAP dubious by direct nPCR were found to be positive by culture-based nPCR and hMRS (Cohort 2), indicating that the pathogen was originally present in the patient's blood (albeit in low amounts) and successfully grew in culture at adequate levels.

The culture-based nPCR, relies on the availability of viable bacteria in the clinical sample that can be grown in culture in sufficient amounts before nPCR. Most clinical microbial diagnostics rely on the growth of the pathogen in culture, before performing the appropriate immunological or PCR tests [35], [36]. Growth can be observed within 12 to 24 hours for fast-growing microorganisms, but for slow-growing intracellular microorganisms like MAP it can take from a week up to several months. Another problem with this technique is that some microorganisms are difficult to culture in the laboratory, which limits their detection. Although highly reliable, culture-based PCR can result in the identification of samples as false-negative, due to the absence of a viable pathogen or the inability of the pathogen to grow in culture. Therefore, it is plausible that samples that might be found to be positive by direct nPCR and hMRS to be identified as negative 12 weeks after by culture-based nPCR. This is common for low bacterial loads of slow-growing microorganisms that require highly specialized media and cultural conditions, whose inadequacy might drastically affect bacterial viability leading to cell death and DNA degradation [37]. These problems in detection with PCR methods are encountered in the detection of any intracellular pathogen, as the pathogen has optimized its adaptation and growth within a host cell. Due to their sensitivity and minimal sample processing, hMRS are capable of circumventing PCR's obstacles and achieving improved clinical diagnosis. Our findings indicate that hMRS can detect an intracellular pathogen's genomic marker in biological fluids (i.e. blood) and tissue homogenates within one hour, where the first 30 minutes are spent on crude DNA extraction and the remaining time on readout.

Figure 6:
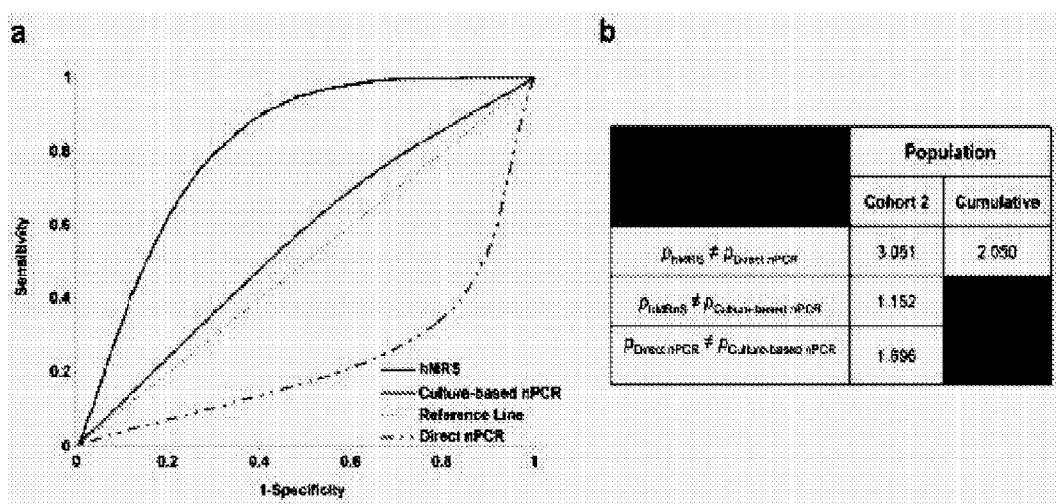
FIG. 6 (a) Blood samples from a second population (Cohort 2, n=26) were screened for the presence of the MAP IS900 genomic element with hMRS, direct nPCR and culture-based nPCR after 12-week cultivation. The receiver operating characteristic (ROC) curve indicated that the hMRS, can better differentiate between symptomatic (Crohn's) and asymptomatic (healthy) states than the two gold standard methods. (b) Two-proportion z-test confirmed hMRS as a better clinical diagnostic utility than the PCR-based methods.

Herein, we have also demonstrated that MAP DNA can be detected in various tissues from Johne's disease animals, as well as in biopsies and blood from Crohn's disease patients, at the epitope and genomic biomarker levels. Furthermore, our results indicate that hMRS can detect the presence of MAP in Crohn's disease patients more reliably than direct or cultured-based nPCR. As a matter of fact, hMRS is a better predictor of the state of the disease, correlating the clinical state of a patient with the presence of MAP in blood samples (FIG. 6). The use of hMRS could be a powerful new tool in the study of the mechanism of infection of intracellular pathogens and its relation to disease state, as well as in elucidating intracellular pathogens' adaptation strategies [38]. Difficulties in detecting MAP hamper studies aimed at the investigation of the potential role of MAP in Crohn's disease pathology, as well as the pathogen's impact on the dairy and beef industries [39]. Overall, these studies provide evidence for the use of hybridizing magnetic nanosensors and magnetic relaxation detection to reliably identify the presence of an intracellular pathogen in clinical samples in a fast, cost-effective and highly sensitive way.

Methods

Preparation of IS900-Specific hMRS

The IS900-specific hMRS were prepared from propargylated polyacrylic-acid-coated iron oxide nanoparticles, utilizing literature available protocols [11]. Specifically, incorporation of propargyl groups on polyacrylic-acid-coated iron oxide nanoparticles was achieved via the carbodiimide chemistry, followed by magnetic separation of the nanoparticles, using an LS25 MACS column (Miltenyi) [11]. Subsequently, the propargyl-functionalized iron oxide nanoparticles were reacted with an azide-modified oligonucleotide, which is complementary to a segment of MAP's IS900 genomic element. Conjugation of the azide-terminated 15-bp oligonucleotide 5'-ATGTGGTTGCTGTGT-3' (SEQ ID NO. 1) was achieved via "click" chemistry, as previously described [40]. Briefly, 400 μL propargylated iron oxide nanoparticles were resuspended in 1,100 μL NaHCO3 buffer (0.1 M, pH 8.4). To this, 200 μL of 10 mM TCEP (tris(2-carboxyethyl)phosphane hydrochloride, Sigma) were added as a reducing agent. Twenty μL of 6.3 M oligo were diluted in 80 μL NaHCO3 buffer (0.1 M, pH 8.4) and added to the nanoparticle solution. The reaction was initiated with the dropwise addition of 150 μL Cu(I)-TBTA complex (tris(benzyltriazolylmethyl)amine, 10 mM, Sigma), which was previously prepared in DI water and tbutanol (9[ratio]1). The reaction was incubated at room temperature under continuous mixing for 3 hours, followed by overnight incubation at 4° C. under constant mixing. The resulting IS900 hMRS were dialyzed against DI water using a 6,000-8,000 MWCO membrane (Spectrum), followed by magnetic separation with an LS25 MACS column (Miltenyi). The epitope-sensing MRS were formulated as previously reported, and the MAP antibody was obtained from Dr. Naser's lab [12]. Briefly, polyacrylic-acid-coated iron oxide nanoparticles were conjugated to Protein G via the EDC/NHS chemistry, in order to have Protein G as a high-affinity immunoglobulin linker that provides optimal antibody orientation [12]. The reaction was performed according to the literature, followed by magnetic separation through a 1×-PBS-equilibrated LS25 column and antibody conjugation [12]. The nanoparticle valency of the antibody-carrying nanoparticles was assessed through quantification of the nanoparticles' protein content, using published methodologies [11]. Size determination of all hMRS was achieved through dynamic light scattering, using the PDDLS CoolBatch 40T instrument and Precision Deconvolve 32 software. Zeta potential measurements were performed on a Malvern zetasizer, while the R1 and R2 relaxivities were determined after determination of the nanoparticle's iron content and relaxation studies on a compact relaxometer (Minispec, Bruker). Determination of the hMRS oligonucleotide concentration was achieved by monitoring the absorbance at 260 and 305 nm (background), using a Nanodrop 1000 spectrophotometer (Thermo Scientific), as previously described [12]. The hMRS were stored at 4° C. until further use.

Bacterial Cultures, Isolates and Homogenized Tissue

Lab strains of MAP and clinical isolates were grown in 12B* BACTEC bottles (Becton Dickinson) as previously described [21]. Quantification of MAP grown in the BACTEC bottles was assessed with the BACTEC 460 TB Analyzer (Becton Dickinson). Heat-inactivation of MAP was performed by autoclaving the BACTEC bottle for 10 mins. *Proteus vulgaris* #8427, *Staphylococcus aureus* #33862, *Pseudomonas aeruginosa* #27853, *Enterococcus faecalis, Escherichia coli* #8739, and *Serratia marcensis* were grown in culture tubes with nutrient broth, and bacterial growth was monitored spectrophotometrically. Heat inactivation of these bacteria was performed by autoclaving the culture tubes for 10 minutes. Upon inactivation, all bacterial stocks were placed in a Fisher Isotemp freezer (Fisher Scientific), until further use. Clinical isolates and tissue specimens from animals with Johne's disease were obtained from tissue collections stored in Dr. Naser's laboratory.

Extraction of Pure and Crude Bacterial DNA from Bacterial Cultures

DNA was extracted from cultured bacteria in a class II biosafety cabinet, according to literature-available procedures [21]. One mL of bacterial cultures was aseptically transferred to microcentrifuge tubes, followed by centrifugation at 13,200 rpm. The resulting pellets were resuspended in 120 μL sterile TE buffer (10 mM Tris, 1 mM EDTA, pH 8.0) and incubated in a dry heat bath at 100° C. Samples without further processing were used as crude DNA extracts in MRnS and nPCR studies. In order to obtain pure bacterial DNA, after heating the samples, we placed them on ice for 15 minutes and then centrifuged them at 12,000 rpm for 10 minutes at 4° C. The supernatants were transferred to Phaselock gel tubes (Eppendorf), which were supplemented with 200 μL of phenol/chloroform/isoamyl alcohol (1:1:24 v:v, Acros). The tubes were centrifuged for 5 minutes (12,000 rpm, 4° C.), and the supernatants were precipitated using 400 μL 100% ethanol cooled to −20° C. The precipitated DNA was washed, dried, and finally reconstituted in 50 μL TE buffer. Pure and crude bacterial DNA was stored at 4° C. until further analysis, whereas spectrophotometric quantification of DNA content was achieved using a compact spectrophotometer (Nanodrop 1000, Thermo Scientific). Crude and pure DNA extractions from clinical isolates were similarly performed.

hMRS and Nested PCR Experiments

Serial dilutions of bacterial DNA were prepared in TE buffer. For the relaxation-mediated experiments, 200 μL of the nanoparticle suspension (6 μg Fe/mL in 0.1 M phosphate buffer, 0.1 M NaCl, pH 7.4) were incubated with 1 μL of bacterial DNA or control (TE buffer). The samples were heated twice for 3 minutes at 95° C. After this, the samples were transferred to relaxometer tubes and cooled down at room temperature, while taking relaxation measurements on a magnetic relaxometer (Minispec, Bruker). For the specificity assays using a complementary synthetic target (5'-TCCTTCGGCCATCCAACACAGCAACCACAT-3' (SEQ ID NO. 2), 1 μL of the target (1.1 M) was added to the hMRS mycobacterial samples containing the same DNA concentration (3.5 ng/μL). Similar DNA concentration was used for the specificity experiment utilizing other Gram-positive and Gram-negative bacteria and hMRS (3 μg Fe/mL). For the sensitivity experiments, serial dilutions of pure and crude MAP DNA were prepared from pure cultures of MAP grown in 12B* BACTEC bottles, which had been processed and quantified as described in the preceding section (DNA extraction methodology). Nested PCR (nPCR) was performed as previously described [21].

Blood Samples, Extraction of Bacterial DNA from White Blood Cells and MAP Culturing Blood samples were collected from healthy individuals and patients with Crohn's disease at the University of Florida, College of Medicine, in accordance to Institutional Review Board guidelines. The samples were coded and sent to the University of Central Florida for blind screening via PCR and hMRS analyses, without knowing in advance the individual's condition, demographics and MAP's presence (Cohorts 1 and 2). Isolation of white blood cells was achieved via centrifugation at 3,000 rpm for 10 minutes at room temperature, as previously described [21]. Pure DNA was extracted via phenol/chloroform/isoamyl alcohol precipitation, similar to previously published methodologies. The pure DNA was subjected to direct nested PCR, as described above. Crude DNA extraction from the isolated white blood cells was achieved via centrifugation at 13,200 rpm for 2 minutes. The resulting pellets were resuspended in 120 μL sterile TE buffer (10 mM Tris, 1 mM EDTA, pH 8.0) and incubated in a dry heat bath at 100° C. for 30 minutes, followed by cooling and centrifugation at 12,000 rpm that provided us with supernatants rich in crude DNA. For bacterial culturing, buffy coat samples were prepared in sterile phosphate buffered saline as described before and inoculated on MGIT bottles. The inoculants were first incubated at 37° C. in a 5% $CO_2$ atmosphere for 12 weeks, and then pure DNA extraction was performed as stated above.

Measurement of Proton Relaxation Times

Spin-spin relaxation times (T2) were measured using a 0.47 T mq20 NMR analyzer (Minispec, Bruker). T2 values were obtained before and after addition of the sample, and through the time course of the study. All T2 measurements were performed using a CPMG pulse-echo train with a 1.5 ms interpulse spacing (Bruker Corp., Billerica, Mass.). The change in magnetic resonance signal ($\Delta$T2+) was defined as the sample's T2 minus the magnetic signal of the corresponding negative control. All experiments and measurements were carried out in triplicate and data were expressed as mean±standard error, unless otherwise denoted.

Statistical Analysis

Clinical diagnosis and sample collection was performed at the College of Medicine, University of Florida, based on clinical and endoscopic criteria [21]. Samples identified as IS900-positive by the hMRS method had an average $\Delta$T2+ higher than 1.5 ms, while positive samples by the nested PCR method had a unique 298-bp nucleotide sequence. The averages of three independent experiments are reported, unless otherwise stated. Two-proportion z-test statistics were determined through the SPSS package, with the confidence level set at 95% (IBM Co.). ROC analysis was performed based on hMRS determination of the sample's MAP load. This was achieved through the correlation of the $\Delta$T2+ signal to bacterial genome copies, using a crude extracted DNA standard curve (FIG. 9). For nPCR, the presence of a band corresponding to IS900 was marked as positive (value=1), whereas its absence was assigned as negative (value=0). The overall ROC methodology was performed as previously reported in literature [34]. Specifically, the classification variable was the individual's clinical condition (Crohn's disease vs healthy), whereas the output curve was fitted using logistic regression.

REFERENCES

1. Batt C A. Materials science. Food pathogen detection. Science. 2007; 316:1579-1580.

2. Ferrari M. Cancer nanotechnology: opportunities and challenges. Nat Rev Cancer. 2005; 5:161-171.
3. Jain K K. Nanotechnology in clinical laboratory diagnostics. Clin Chim Acta. 2005; 358:37-54.
4. Rosi N L, Mirkin C A. Nanostructures in biodiagnostics. Chem. Rev. 2005; 105:1547-1562.
5. Kaittanis C, Santra S, Perez J M. Emerging nanotechnology-based strategies for the identification of microbial pathogenesis. Adv Drug Deliv Rev. 2010; 62:408-423.
6. Gao L, Zhuang J, Nie L, Zhang J, Zhang Y, et al. Intrinsic peroxidase-like activity of ferromagnetic nanoparticles. Nat. Nanotechnol. 2007; 2:577-583.
7. Gao J, Gu H, Xu B. Multifunctional magnetic nanoparticles: design, synthesis, and biomedical applications. Acc Chem. Res. 2009; 42:1097-1107.
8. Gaster R S, Xu L, Han S J, Wilson R J, Hall D A, et al. Quantification of protein interactions and solution transport using high-density GMR sensor arrays. Nat. Nanotechnol. 2011; 6:314-320.
9. Kaittanis C, Naser S A, Perez J M. One-step, nanoparticle-mediated bacterial detection with magnetic relaxation. Nano Lett. 2007; 7:380-383.
10. Laurent S, Bridot J L, Elst L V, Muller R N. Magnetic iron oxide nanoparticles for biomedical applications. Future Med. Chem. 2010; 2:427-449.
11. Kaittanis C, Santra S, Perez J M. Role of nanoparticle valency in the nondestructive magnetic-relaxation-mediated detection and magnetic isolation of cells in complex media. J Am Chem. Soc. 2009; 131:12780-12791.
12. Kaittanis C, Santra S, Santiesteban O J, Henderson T J, Perez J M. The Assembly State between Magnetic Nanosensors and Their Targets Orchestrates Their Magnetic Relaxation Response. J Am Chem. Soc. 2011; 133: 3668-3676.
13. Grossman H L, Myers W R, Vreeland V J, Bruehl R, Alper M D, et al. Detection of bacteria in suspension by using a superconducting quantum interference device. Proc Natl Acad Sci USA. 2004; 101:129-134.
14. Wang S X, Li G. Advances in Giant Magnetoresistance Biosensors With Magnetic Nanoparticle Tags: Review and Outlook. IEEE TRANSACTIONS ON MAGNETICS. 2008; 44:1687-1702.
15. Cocito C, Gilot P, Coene M, de Kesel M, Poupart P, et al. *Paratuberculosis*. Clin Microbiol Rev. 1994; 7:328-345.
16. Chiodini R J. Crohn's disease and the mycobacterioses: a review and comparison of two disease entities. Clin Microbiol Rev. 1989; 2:90-117.
17. Dalziel T K. Chronic Interstitial Enteritis. The British Medical Journal. 1913; 2:1068-1070.
18. Crohn B B, Ginzburg L, Oppenheimer G D. REGIONAL ILEITIS. Journal of the American Medical Association. 1932; 99:1323-1329.
19. Greenstein R J, Greenstein A J. Is there clinical, epidemiological and molecular evidence for two forms of Crohn's disease? Mol Med. Today. 1995; 1:343-348.
20. Chiodini R J, Van Kruiningen H J, Thayer W R, Coutu J A. Spheroplastic phase of mycobacteria isolated from patients with Crohn's disease. J Clin Microbiol. 1986; 24:357-363.
21. Naser S A, Ghobrial G, Romero C, Valentine J F. Culture of *Mycobacterium avium* subspecies *paratuberculosis* from the blood of patients with Crohn's disease. Lancet. 2004; 364:1039-1044.
22. Romero C, Hamdi A, Valentine J F, Naser S A. Evaluation of surgical tissue from patients with Crohn's disease for the presence of *Mycobacterium avium* subspecies *paratuberculosis* DNA by in situ hybridization and nested polymerase chain reaction. Inflamm Bowel Dis. 2005; 11:116-125.
23. Green E P, Tizard M L, Moss M T, Thompson J, Winterbourne D J, et al. Sequence and characteristics of IS900, an insertion element identified in a human Crohn's disease isolate of *Mycobacterium paratuberculosis*. Nucleic Acids Res. 1989; 17:9063-9073.
24. Lisby G, Andersen J, Engbaek K, Binder V. *Mycobacterium paratuberculosis* in intestinal tissue from patients with Crohn's disease demonstrated by a nested primer polymerase chain reaction. Scand J. Gastroenterol. 1994; 29:923-929.
25. Sanderson J D, Moss M T, Tizard M L, Hermon-Taylor J. *Mycobacterium paratuberculosis* DNA in Crohn's disease tissue. Gut. 1992; 33:890-896.
26. Cutler J I, Zhang K, Zheng D, Auyeung E, Prigodich A E, et al. Polyvalent nucleic acid nanostructures. J Am Chem. Soc. 2011; 133:9254-9257.
27. Fang Y, Wu W H, Pepper J L, Larsen J L, Marras S A, et al. Comparison of real-time, quantitative PCR with molecular beacons to nested PCR and culture methods for detection of *Mycobacterium avium* subsp. *paratuberculosis* in bovine fecal samples. J Clin Microbiol. 2002; 40:287-291.
28. Hiratsuka S, Watanabe A, Aburatani H, Maru Y. Tumour-mediated upregulation of chemoattractants and recruitment of myeloid cells predetermines lung metastasis. Nat Cell Biol. 2006; 8:1369-1375.
29. Morgan R A, Dudley M E, Wunderlich J R, Hughes M S, Yang J C, et al. Cancer regression in patients after transfer of genetically engineered lymphocytes. Science. 2006; 314:126-129.
30. Kruse J P, Gu W. Modes of p53 regulation. Cell. 2009; 137:609-622.
31. Naser S A, Shafran I, Schwartz D, El-Zaatari F, Biggerstaff J. In situ identification of mycobacteria in Crohn's disease patient tissue using confocal scanning laser microscopy. Mol Cell Probes. 2002; 16:41-48.
32. Grimm J, Perez J M, Josephson L, Weissleder R. Novel nanosensors for rapid analysis of telomerase activity. Cancer Res. 2004; 64:639-643.
33. Perez J M, Grimm J, Josephson L, Weissleder R. Integrated nanosensors to determine levels and functional activity of human telomerase. Neoplasia. 2008; 10:1066-1072.
34. Haun J B, Castro C M, Wang R, Peterson V M, Marinelli B S, et al. Micro-NMR for rapid molecular analysis of human tumor samples. Sci Transl Med. 3:71ra16.
35. Bancroft E A. Antimicrobial resistance: it's not just for hospitals. Jama. 2007; 298:1803-1804.
36. Taubes G. The bacteria fight back. Science. 2008; 321: 356-361.
37. Engelberg-Kulka H, Amitai S, Kolodkin-Gal I, Hazan R. Bacterial programmed cell death and multicellular behavior in bacteria. PLoS Genet. 2006; 2:e135.
38. Homolka S, Niemann S, Russell D G, Rohde K H. Functional genetic diversity among *Mycobacterium tuberculosis* complex clinical isolates: delineation of conserved core and lineage-specific transcriptomes during intracellular survival. PLoS Pathog. 2010; 6:e1000988.
39. Pierce E S. Where are all the *Mycobacterium avium* subspecies *paratuberculosis* in patients with Crohn's disease? PLoS Pathog. 2009; 5:e1000234.
40. Seela F, Sirivolu V R. Nucleosides and oligonucleotides with diynyl side chains: the huisgen-sharpless cycloaddition "click reaction" performed on DNA and their constituents. Nucleosides Nucleotides Nucleic Acids. 2007; 26:597-601.

The invention claimed is:

1. A method of detecting a nucleic acid analyte of interest in a sample, the method comprising:
   (a) contacting nucleic acid from a sample with a hybridizing magnetic relaxation nanosensor (hMRS) comprising a plurality of nucleic acid sequence probes configured to specifically hybridize to one unique sequence of the nucleic acid analyte of interest, so that only one hMRS hybridizes per nucleic acid analyte of interest; and
   (b) detecting a change in the magnetic resonance signal from a hMRS hybridized to a nucleic acid analyte of interest in the nucleic acid from the sample; thereby detecting the presence of the nucleic acid analyte of interest in the sample.

2. The method of claim 1, further comprising the step of isolating nucleic acid from the sample to obtain isolated nucleic acid.

3. The method of claim 2, wherein said contacting nucleic acid from the sample comprises contacting isolated nucleic acid with at least one hMRS.

4. The method of claim 1, wherein said sample is any sample harboring microorganisms from clinical or environmental sources.

5. The method of claim 1, wherein the nucleic acid analyte of interest is of a microorganism.

6. The method of claim 5, wherein the microorganism is a strain of bacteria.

7. The method of claim 6, wherein the bacteria is a *Mycobacterium*, and wherein the *Mycobacterium* is *Mycobacterium avium* spp. *Paratuberculosis*.

8. The method of claim 5, wherein said nucleic acid analyte of interest is DNA or RNA sequence of a microorganism.

9. The method of claim 8, wherein said nucleic acid analyte of interest is IS900 nucleotide sequence specific to MAP.

10. The method of claim 1, wherein said hMRS comprises a magnetic nanoparticle.

11. The method of claim 10, wherein said magnetic nanoparticle comprises a metal or metal oxide.

12. The method of claim 1, wherein said method can detect the presence of a nucleic acid analyte of interest within 90 minutes or less.

13. A hybridizing magnetic relaxation nanosensor (hMRS), comprising a magnetic nanoparticle associated with a plurality of nucleic acid probes configured to specifically hybridize to one unique sequence of a nucleic acid analyte of interest, so that only one hMRS hybridizes per nucleic acid analyte of interest.

14. The hMRS of claim 13, wherein said magnetic nanoparticle comprises a metal or metal oxide.

15. The hMRS of claim 13, wherein said magnetic nanoparticle comprises iron oxide.

16. The hMRS of claim 13, wherein said nucleic acid analyte of interest is of a microorganism.

17. The hMRS of claim 16, wherein said microorganism is a strain of bacteria.

18. The hMRS of claim 17, wherein said bacteria is a *Mycobacterium*, and wherein said *Mycobacterium* is *Mycobacterium avium* spp. *Paratuberculosis*.

* * * * *

UNITED STATES PATENT AND TRADEMARK OFFICE
CERTIFICATE OF CORRECTION

| | |
|---|---|
| PATENT NO. | : 9,109,249 B2 |
| APPLICATION NO. | : 14/118834 |
| DATED | : August 18, 2015 |
| INVENTOR(S) | : Saleh Naser, Jesus Manuel Perez and Charalambos Kaittanis |

It is certified that error appears in the above-identified patent and that said Letters Patent is hereby corrected as shown below:

In the Specification,

The following paragraph should be inserted at Column 1, line 4 --This invention was made with Government support under agency contract/grant no. R01 GM084331 awarded by the National Institutes of Health. The government has certain rights in the invention.--

Signed and Sealed this
Second Day of August, 2016

Michelle K. Lee
*Director of the United States Patent and Trademark Office*

SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: synthetic construct; azide modified
      oligonucleotide

<400> SEQUENCE: 1
atgtggttgc tgtgt                                                    15

<210> SEQ ID NO 2
<211> LENGTH: 30
<212> TYPE: DNA
<213> ORGANISM: Artificial Sequence
<220> FEATURE:
<223> OTHER INFORMATION: synthetic construct; oligonucleotide

<400> SEQUENCE: 2
tccttcggcc atccaacaca gcaaccacat                                    30